United States Patent
Dixon et al.

(10) Patent No.: US 10,420,690 B2
(45) Date of Patent: Sep. 24, 2019

(54) MONITORING SYSTEMS DEVICES AND METHODS FOR PATIENT LIFTS

(71) Applicant: Liko Research & Development AB, Lulea (SE)

(72) Inventors: Steven A. Dixon, Cincinnati, OH (US); David Ribble, Indianapolis, IN (US)

(73) Assignee: Liko Research & Development AB, Luleå (SE)

( * ) Notice: Subject to any disclaimer, the term of this patent is extended or adjusted under 35 U.S.C. 154(b) by 1031 days.

(21) Appl. No.: 13/941,161

(22) Filed: Jul. 12, 2013

(65) Prior Publication Data

US 2014/0013503 A1    Jan. 16, 2014

Related U.S. Application Data

(60) Provisional application No. 61/671,048, filed on Jul. 12, 2012, provisional application No. 61/801,492, (Continued)

(51) Int. Cl.
*A61G 7/10*   (2006.01)
*A61G 7/018*  (2006.01)
(Continued)

(52) U.S. Cl.
CPC ........... *A61G 7/1073* (2013.01); *A61G 7/018* (2013.01); *A61G 7/108* (2013.01); *A61G 7/1017* (2013.01);
(Continued)

(58) Field of Classification Search
CPC ...... A61G 7/10; A61G 7/1001; A61G 7/1015; A61G 7/1017; A61G 7/1023;
(Continued)

(56) References Cited

U.S. PATENT DOCUMENTS 4,944,056 A * 7/1990 Schroeder ............ A61G 7/1015
 5/85.1
6,289,534 B1 * 9/2001 Hakamiun ........... A61G 7/1017
 5/83.1

(Continued)

FOREIGN PATENT DOCUMENTS

WO   2007075701 A2   7/2007
WO   2010141865 A1   12/2010

OTHER PUBLICATIONS

Letter dated Sep. 15, 2014 From Ari M. Bai with Polsinelli; One East Street, Suite 1200; Phoenix, AZ 85004-2568 RE: U.S. Appl. No. 13/941,161 Monitoring Systems Devices and Methods for Patient Lift. Refers to U.S. Pat. No. 8,538,710 and US Publication No. 2014/0013503.

(Continued)

*Primary Examiner* — Peter M. Cuomo
*Assistant Examiner* — David R Hare
(74) *Attorney, Agent, or Firm* — Dinsmore & Shohl LLP

(57) ABSTRACT

A monitoring system comprises a lift assembly configured to lift a patient; a control system configured to control operation of the lift system; and a reporting system in communication with the control system and configured to receive operational information for the lift assembly. The reporting system compares the operational information to a predetermined set of values to determine if the operation of the lift is in compliance with the protocols.

15 Claims, 26 Drawing Sheets

Related U.S. Application Data filed on Mar. 15, 2013, provisional application No. 61/798,207, filed on Mar. 15, 2013.

(51) Int. Cl.
  *G16H 40/63* (2018.01)
  *A61B 5/11* (2006.01)

(52) U.S. Cl.
  CPC ......... *A61G 7/1042* (2013.01); *A61G 7/1051* (2013.01); *A61G 7/1061* (2013.01); *A61G 7/1065* (2013.01); *G16H 40/63* (2018.01); *A61B 5/11* (2013.01); *A61B 2562/0257* (2013.01); *A61G 2203/12* (2013.01); *A61G 2203/20* (2013.01); *A61G 2203/44* (2013.01); *A61G 2203/72* (2013.01)

(58) Field of Classification Search
  CPC .. A61G 7/1051; A61G 7/1063; A61G 7/1065; A61G 7/1073; A61G 7/108; A61G 2203/22; A61G 2203/30; A61G 2203/36; A61G 2203/80; A61G 2203/72; A61G 2203/44; A61G 2203/20; A61G 2203/12; G16H 40/63; A61B 2562/0257; A61B 5/11
  See application file for complete search history.

(56) References Cited

U.S. PATENT DOCUMENTS

| | | | | |
|---|---|---|---|---|
| 6,523,195 | B1* | 2/2003 | Rodier | A61G 7/1015 |
| | | | | 104/89 |
| 7,240,621 | B2* | 7/2007 | Chepurny | A61G 7/1015 |
| | | | | 104/173.1 |
| 8,538,710 | B2 | 9/2013 | Todd | |
| 8,910,325 | B2* | 12/2014 | Faucher | A61G 7/1042 |
| | | | | 212/278 |
| 2009/0049610 | A1* | 2/2009 | Heimbrock et al. | 5/600 |
| 2010/0097181 | A1* | 4/2010 | Sorensen | A61G 7/10 |
| | | | | 340/10.1 |
| 2010/0192296 | A1* | 8/2010 | Clough | A61G 7/1005 |
| | | | | 5/83.1 |
| 2010/0217618 | A1 | 8/2010 | Piccirillo et al. | |
| 2010/0224841 | A1* | 9/2010 | Liljedahl | A61G 7/1017 |
| | | | | 254/120 |
| 2011/0035058 | A1* | 2/2011 | Clough | A61G 7/1065 |
| | | | | 700/275 |
| 2011/0301440 | A1* | 12/2011 | Riley | A61B 5/02055 |
| | | | | 600/301 |
| 2012/0095777 | A1 | 4/2012 | Chang et al. | |
| 2013/0019401 | A1 | 1/2013 | Faucher et al. | |
| 2013/0076517 | A1* | 3/2013 | Penninger et al. | 5/600 |
| 2013/0091631 | A1* | 4/2013 | Hayes | A61G 7/002 |
| | | | | 5/600 |
| 2013/0253291 | A1* | 9/2013 | Dixon et al. | 5/425 |
| 2013/0319775 | A1* | 12/2013 | Ngoh | A61G 7/108 |
| | | | | 177/1 |
| 2014/0013503 | A1 | 1/2014 | Dixon et al. | |
| 2014/0115778 | A1* | 5/2014 | Ng | A61G 7/1015 |
| | | | | 5/83.1 |

OTHER PUBLICATIONS

Claim Chart for U.S. Patent Application Publication No. 2014/0013503 ('503 Application), Dixon et al. Monitoring Systems Devices and Methods for Patient Lifts and U.S. Pat. No. 8,538,710 (the '710 Patent) Todd et al. Methods and Systems for Monitoring Lift Usage.

Unirope LTD; RFID Tags; [retrieved online on Jul. 11, 2013], http://www.unirope.com/chainmeshslings/rfid_tags_shtml. pp. 1-2.

LiftAll; RFID Tagging; [online], www.lift-all.com; (Nov. 2009). p. 1.

Extended European Search Report & Written Opinion dated Feb. 27, 2015 relating to EP Patent Application No. 13176406.0. pp. 1-12.

Non-Final Office Action dated Sep. 10, 2015 relating to U.S. Appl. No. 13/941,179, filed Jul. 12, 2013. pp. 1-9.

\* cited by examiner

Home Screen

Clinical     Welcome A. Nurse   Logout   Help

Home   Patients   Rooms   Staff   Protocols   Reports

Unit 6 West

| Room | Patient | Protocol | Primary Caregiver | Bed Exit | Bed Rails | Bed Low | Brake on | HOB | Lift battery | Daily Lift events | Lift Emerg. |
|---|---|---|---|---|---|---|---|---|---|---|---|
| 100 | Bob Jones | ---- | Nancy Caregiver | ◯ | ▦ | ◯ | ◯ | 35 | 50% | 20 | ▯ |
| 101 | Jane Doe | Lift | Nancy Caregiver | ◯ | ▦ | ◯ | ◯ | 30 | 90 | 4 | |
| 102 | Roger Dodger | Falls | Doris Day | ⚠ | ▦ | ◯ | ◯ | 5 | 100 | 11 | ▲ |

FIG. 22

Protocols Screen

| Clinical | | | | | Welcome A. Nurse   Logout   Help |
|---|---|---|---|---|---|
| Home | Patients | Rooms | Staff | Protocols | Reports |

Unit 6 West Protocols

Lift

- ☐ Alert when battery status is below ____ %
- ☐ Alert if service is overdue by ____ days
- ☐ Alert if ____ % safe working load has been exceeded
- ☐ Alert if emergency cord is activated
- ☐ Remind service is due in ____ weeks
- ☐ Remind when lift has not been cleaned
- ☐ Remind when battery status is below ____ %

- ⊙ Automatically assign to all lifts
- ⊙ Automatically assign to all lifts
- ⊙ Automatically assign to all lifts
- ⊙ Send alert through Nurse Call system
- ⊙ Automatically notify service group
- ⊙ Automatically notify house keeping
- ⊙ Automatically notify assigned caregiver

Sling

- ☐ Alert if not in room for ____ days
- ☐ Alert if past lifetime expectancy by ____ months
- ☐ Alert if wrong sling is used
- ☐ Remind when periodic inspection is due

- ⊙ Show location of nearest sling
- ⊙ Automatically assign to all slings
- ⊙ Automatically notify service group

FIG. 25

Reporting Screen

| Clinical | | | | Welcome A. Nurse  Logout  Help |
|---|---|---|---|---|
| Home  Patients  Rooms  Staff  Protocols  Reports | | | | |

Reports

| Title | Description | Last Run Date | Notification List | Schedule Interval | On Day | At Time | |
|---|---|---|---|---|---|---|---|
| Protocol Compliance | Percent of time that lifts were in compliance with assigned protocol | 11/02/12 | Charge Nurse | Weekly | Monday | 12:00AM | View/ Edit |
| High Risk Patients | Number of patients and staff time in room | 11/02/12 | Charge Nurse | Weekly | Monday | 12:00AM | View/ Edit |
| Therapy Compliance | Track patient mobility progress using patient lifts | 11/02/12 | Therapy Nurse | Weekly | Wed | 12:00AM | View/ Edit |

FIG. 26

MONITORING SYSTEMS DEVICES AND METHODS FOR PATIENT LIFTS

BACKGROUND OF THE DISCLOSURE

This disclosure relates to monitoring systems, and more particularly, but not exclusively, one contemplated embodiment relates systems, methods, and devices for monitoring, among other things, operational characteristics of a patient lift, compliance with care facility protocols, and patient information and progress. While various systems, methods and devices have been developed, there is still room for improvement. Thus, a need persists for further contributions in this area of technology.

SUMMARY OF THE DISCLOSURE

According to one contemplated embodiment of the disclosure, a monitoring system comprises a lift assembly configured to lift a patient; a control system configured to control operation of the lift system; and a reporting system in communication with the control system and configured to receive operational information for the lift assembly. The reporting system compares the operational information to a predetermined set of values to determine if the operation of the lift is in compliance with the protocols.

In another contemplated embodiment, a person support lifting system comprises a lift assembly configured to lift a person; a sensor coupled to the lift assembly and configured to sense the amount of load generated by the person and supported by the lift assembly; a control system electrically coupled to the sensor configured to display the total of load supported by the lift assembly over a predetermined period of time.

In another contemplated embodiment, a system for associating assets comprises a lift assembly configured to lift a patient; a RFID reading device coupled to the lift assembly; a RFID tag coupled to an asset; and a control system configured to associate the lift assembly and the asset when the asset is less than a predetermined distance from the RFID reading device.

Additional features, which alone or in combination with any other feature(s), such as those listed above and/or those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

Referring now to the illustrative examples in the drawings, wherein like numerals represent the same or similar elements throughout:

FIG. 22 is a screen shot of the interface to the workflow automation system of FIG. 1 showing the home tab, which displays a summary of the status of a hospital bed and lift in the room associated with the patient;

FIG. 25 is a screen shot of the interface to the workflow automation system of FIG. 1 showing the protocols tab, which displays various alert and reminder options for the lifts and slings along with options for how and to whom the alert and/or reminder is to be communicated; and FIG. 26 is a screen shot of the interface to the workflow automation system of FIG. 1 showing the reports tab, which displays a list of caregiver defined (or default) reports that the caregiver can run to filter data collected by the system, along with information about each report and usage statistics.

DETAILED DESCRIPTION OF THE DRAWINGS

Figure 1:
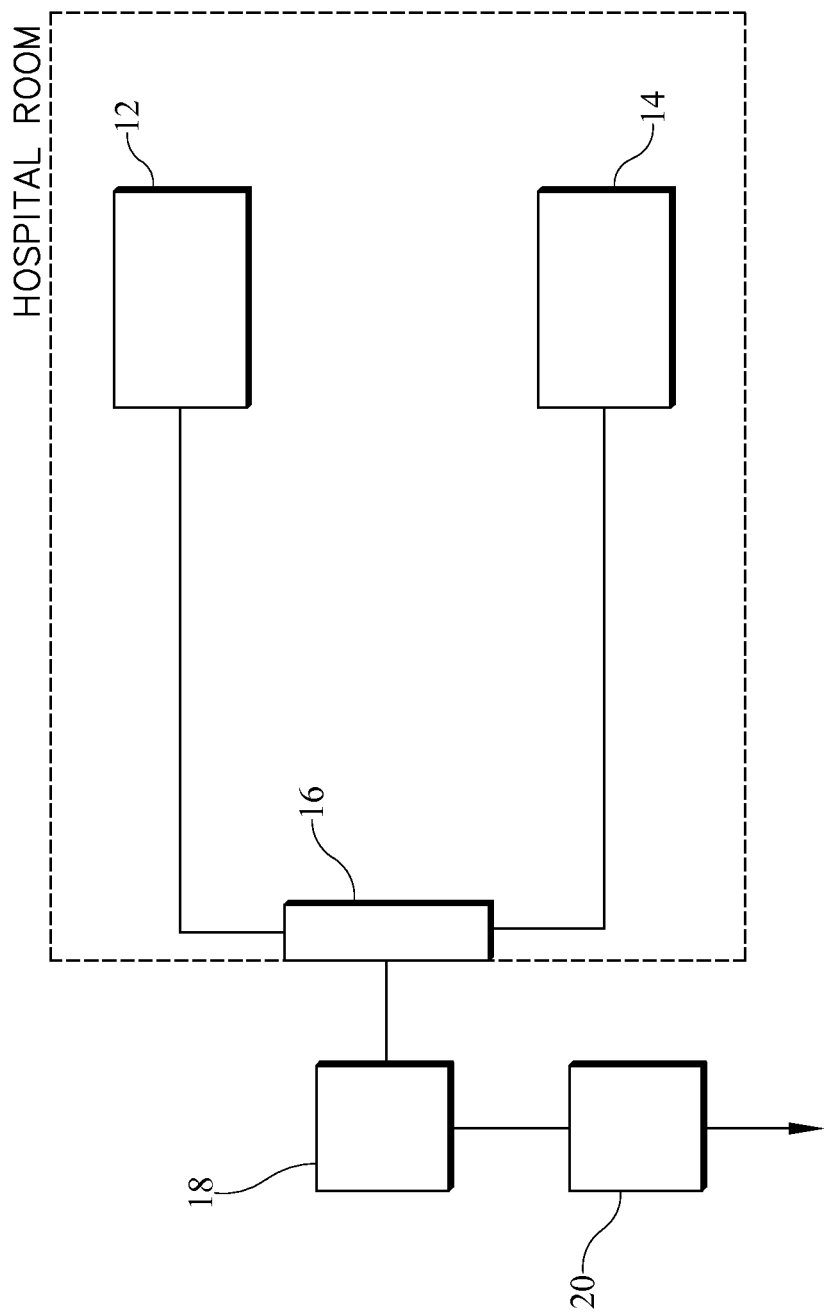
FIG. 1 is a diagrammatic view of a monitoring system according to one contemplated embodiment of this disclosure including a person lift and a hospital bed connected through a room control board to a workflow automation system and hospital network.

While the present disclosure can take many different forms, for the purpose of promoting an understanding of the principles of the disclosure, reference will now be made to the embodiments illustrated in the drawings, and specific language will be used to describe the same. No limitation of the scope of the disclosure is thereby intended. Various alterations, further modifications of the described embodiments, and any further applications of the principles of the disclosure, as described herein, are contemplated.

A monitoring system 10 according to one contemplated embodiment is shown in FIGS. 1-18. The system 10 is configured to assist with training and tracking and reporting information related to at least one of the following: the performance and/or the usage characteristics of the equipment (i.e., the number of times the equipment is used, the duration of use, the number of times the equipment should have been used and was not used, whether the equipment is being operated beyond its safe working parameters, and other performance and/or usage information), the status and/or condition of the equipment (i.e., whether it is damaged, whether it requires routine service or needs to be inspected, whether it is operating within acceptable use parameters, whether the equipment is in use, has an alarm been triggered, and other condition and/or status information), the location of caregivers, equipment, and patients, the room status (i.e., available, occupied, restricted, etc.), information the patient's identification and physiological information, and the care facility's protocols (i.e., what protocols apply to the patient, whether or not use of the equipment is in compliance with the protocols.

The system 10 includes a patient lift system 12 or lift 12, a patient support system 14, a communication system 16, an information management system 18, and hospital network 20 as shown in FIG. 1. The lift system 12 and patient support system 14 are electrically coupled to the communication system 16, which provides for communication between the lift system 12, the patient support system 14, the information management system 18, and the hospital network 20. In one contemplated embodiment, the lift system 12 and the person support system 14 are connected to the communication system 16 via a wired connection. In another contemplated embodiment, the lift system 12 and the person support system 14 communicate with the communication system 16 wirelessly. In another contemplated embodiment, the lift system 12 communicates with the communication system 16 through the communication system of the person support system 14.

Figure 2:
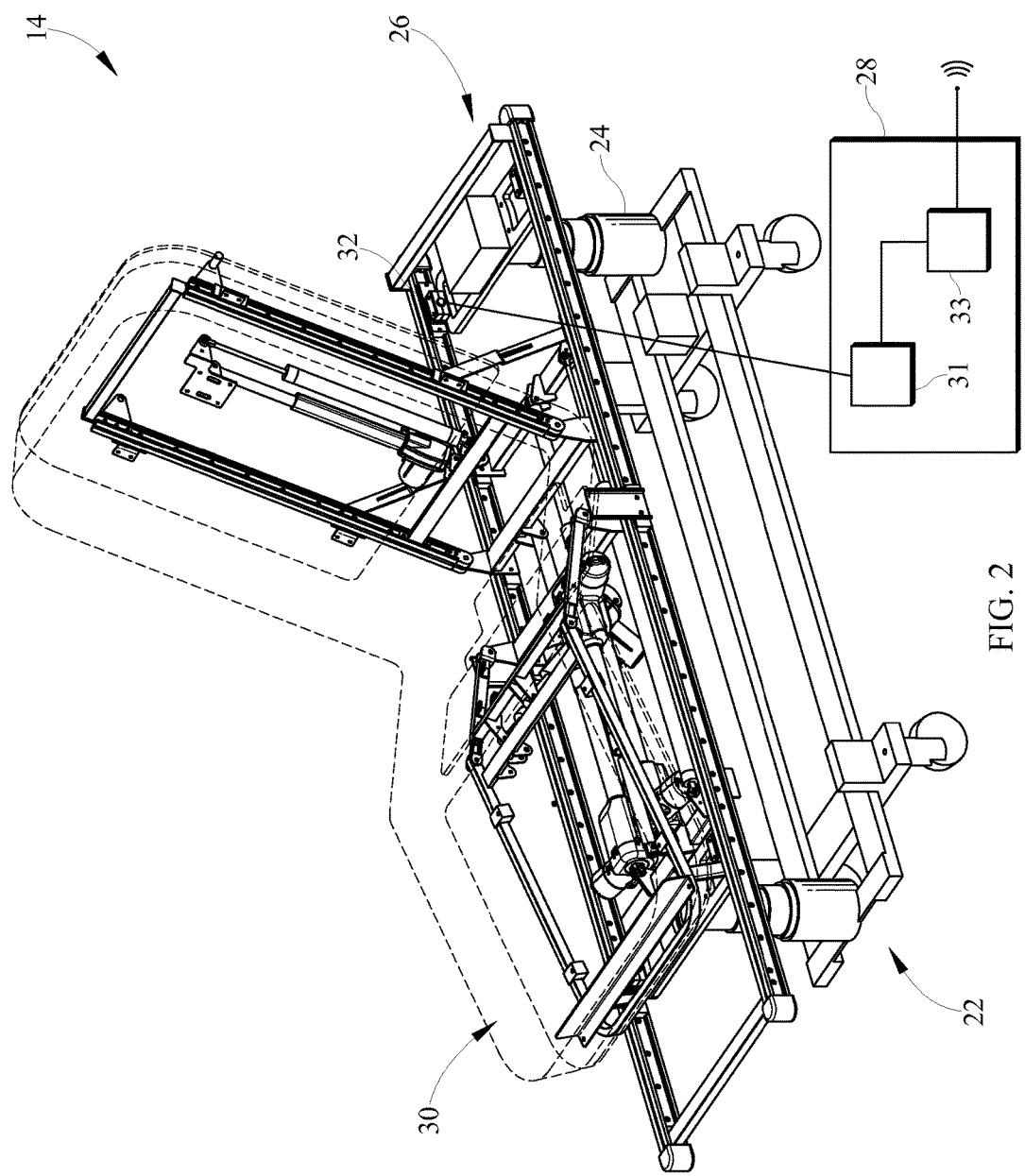
FIG. 2 is a perspective view of the person support system of FIG. 1 showing the upper frame, the lower frame, the lift mechanisms, the control system, and the mattress.

The person support system 14 includes a lower frame 22, a lift mechanism 24 coupled to the lower frame 22, an upper frame 26 movably supported above the lower frame 22 on the lift mechanism 24, a control system 28, and a mattress 30 supported on the upper frame 26 as shown in FIG. 2. In one contemplated embodiment, the patient support system 14 is a hospital bed. In other contemplated embodiments, the patient support system 14 can be a wheelchair, stretcher, or other patient support device. The control system 28 is configured to cause the person support system 14 to perform various functions. In some contemplated embodiments, the control system 28 controls the operation of the lift mechanism 24, gas supplies, motors, and other features of the person support system 14.

The control system 28 includes a controller 31, sensing elements 32, and a communication device 33. In one contemplated embodiment, the sensing element 32 includes a load cell coupled between the upper frame 26 and the lift mechanism 24. In one contemplated embodiment, the controller 31 receives signals from the load cell and determines the weight of an occupant supported on the upper frame 26. In another contemplated embodiment, the controller 31 determines the center of gravity of the occupant supported on the upper frame 26. In another contemplated embodiment, the controller 31 determines the position of the occupant supported on the upper frame 26 using information from the load cells. In some contemplated embodiments, the controller 31 determines the position of the occupant on the upper frame 26 as a function of the occupant's center of gravity. In some contemplated embodiments, the controller 31 determines the occupant's position based on information from a pressure sensing topper. In some contemplated embodiments, the controller 31 determines the occupant's position based on the gas pressure in bladders in a powered mattress 30.

The communication device 33 is configured to communicate information between the person support system 14, the lift system 12 and/or other equipment in the vicinity, the communication system 16, and the hospital network 20. In some contemplated embodiments, the communication device 33 serves as a hub for a room and information from other devices in the room is sent to the communication device 33 to be stored in memory on the person support system 14, or communicated to the communication system 16 or hospital network 20. In some contemplated embodiments, the communication device 33 communicates wirelessly with the communication system 16, other equipment in the room (including the lift system 12) and/or the hospital network 20. In other contemplated embodiments, the communication device communicates via a wired connection with the communication system 16, other equipment in the room (including the lift system 12) and/or the hospital network 20.

Figure 3:
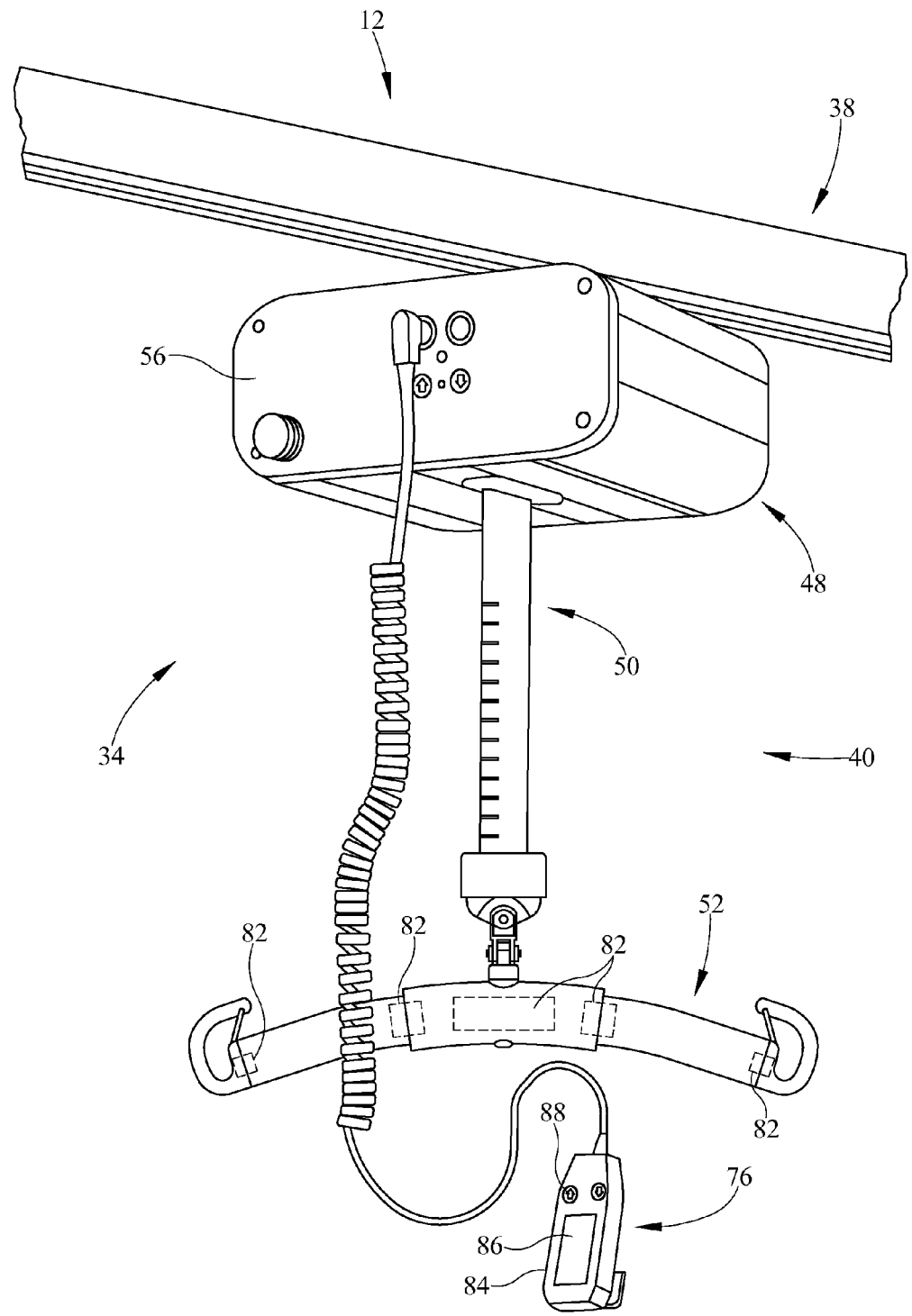
FIG. 3 is a side perspective view of the overhead person lift of FIG. 1 according to one contemplated embodiment.
Figure 4:
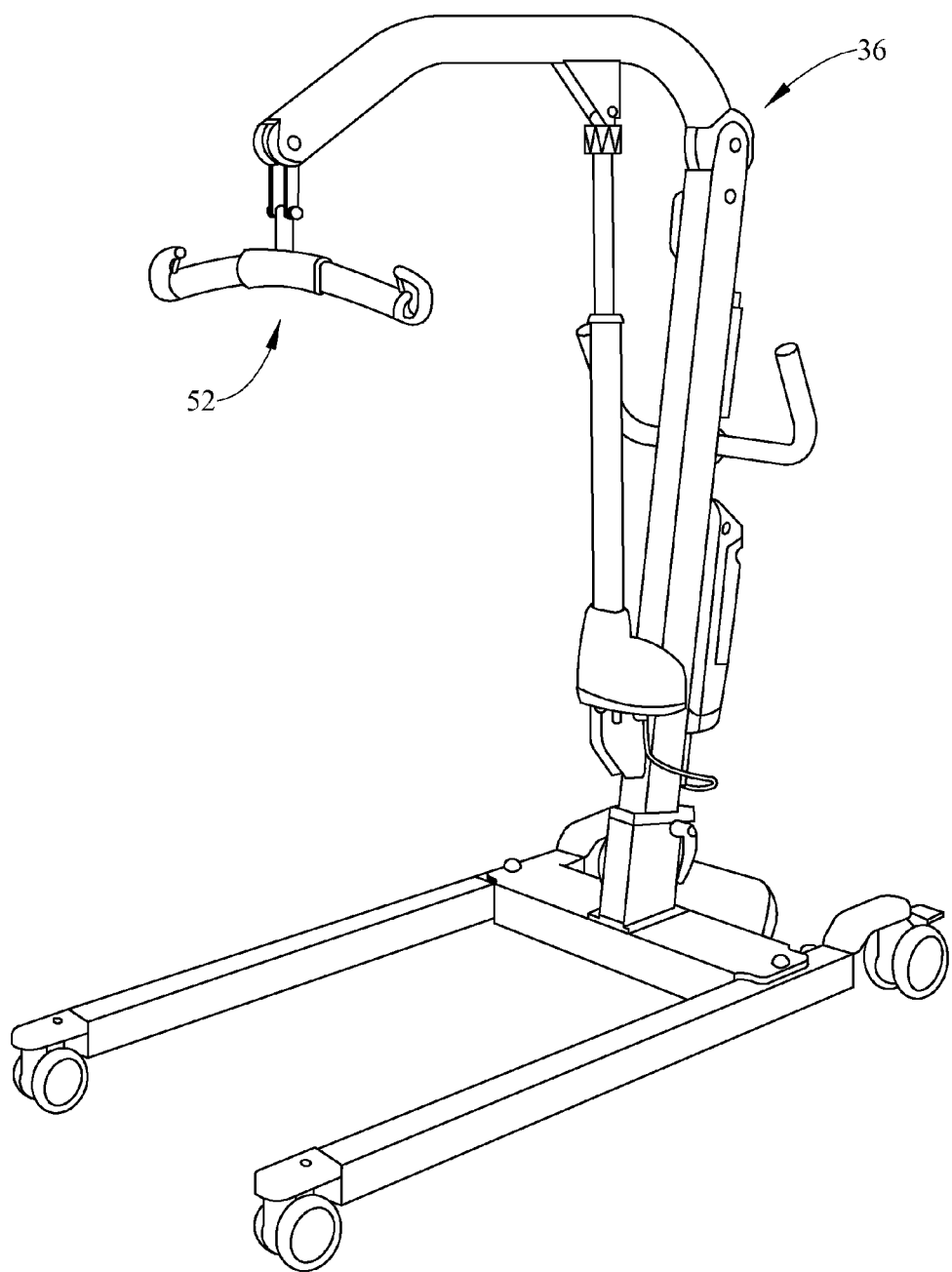
FIG. 4 is a side perspective view of a powered sit-to-stand person lift of FIG. 1 according to one contemplated embodiment.

The lift system 12, according to one contemplated embodiment, includes an overhead lift system 34 as shown in FIG. 3. In some contemplated embodiments, the lift system 12 includes a floor lift system 36 (i.e., a powered sit-to-stand lift) shown in FIG. 4, or other person lifting devices, including the various person lifting devices sold by Liko. The lift system 12 includes a rail 38 coupled to a ceiling of a room and a lift assembly 40 configured to move along the rail 38. The rail 38 includes a track 42, a stop 44 coupled to the track 42, and a conductor 46 along the track 42. In one contemplated embodiment, data and power are communicated over the conductor 46, which can allow a power source in the lift assembly 40 to be recharged, and can allow the lift assembly 40 to communicate with the person support system 14, the communication system 16, and/or the hospital network 20. In some contemplated embodiments, portions of the rail 38 and lift assembly 40 are constructed as disclosed in U.S. Patent Publication No. 2012/0000876, which is incorporated herein by reference.

Figure 5:
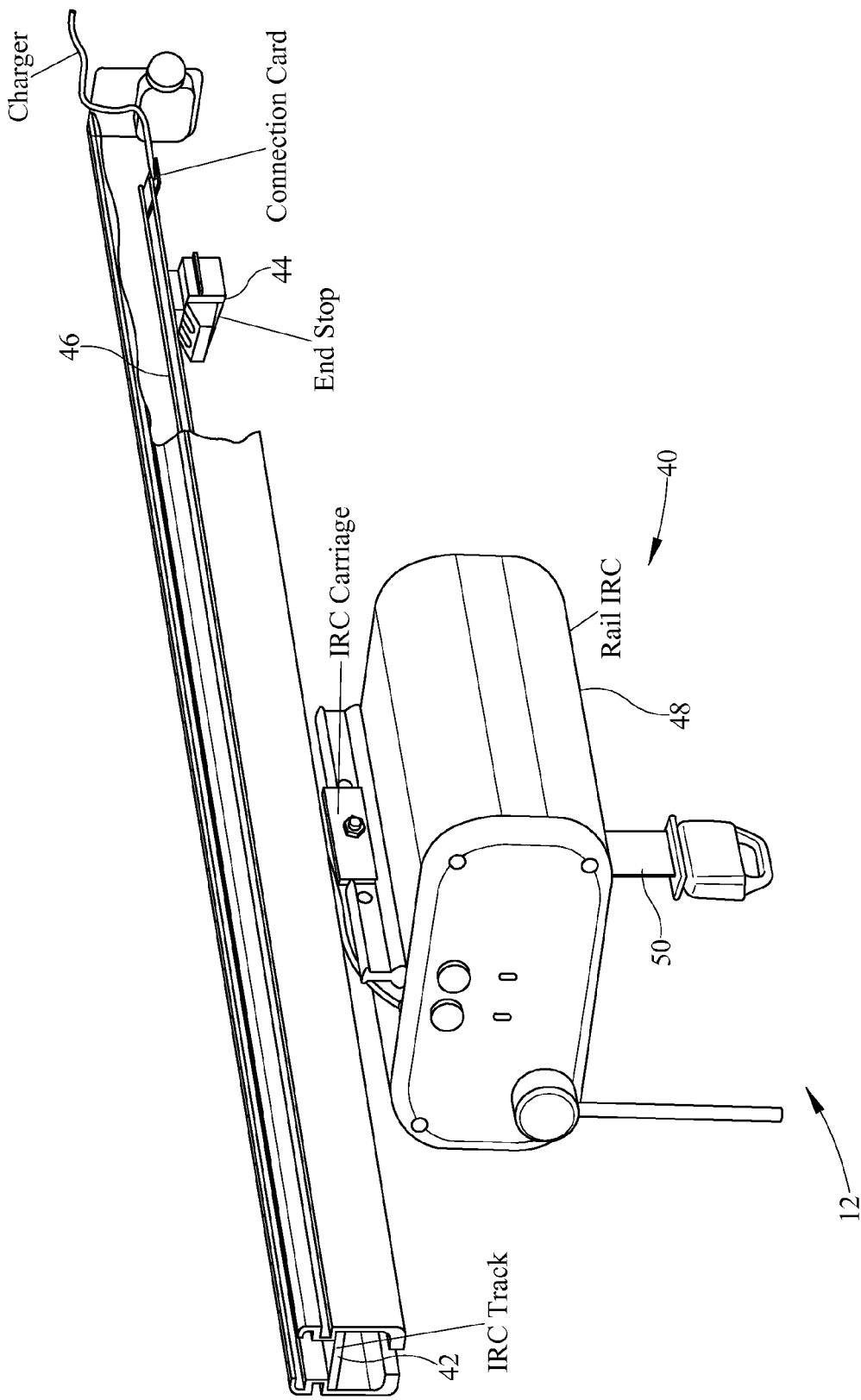
FIG. 5 is a perspective view of the lift system of FIG. 3 showing the lift assembly movably engaging the track.
Figure 6:
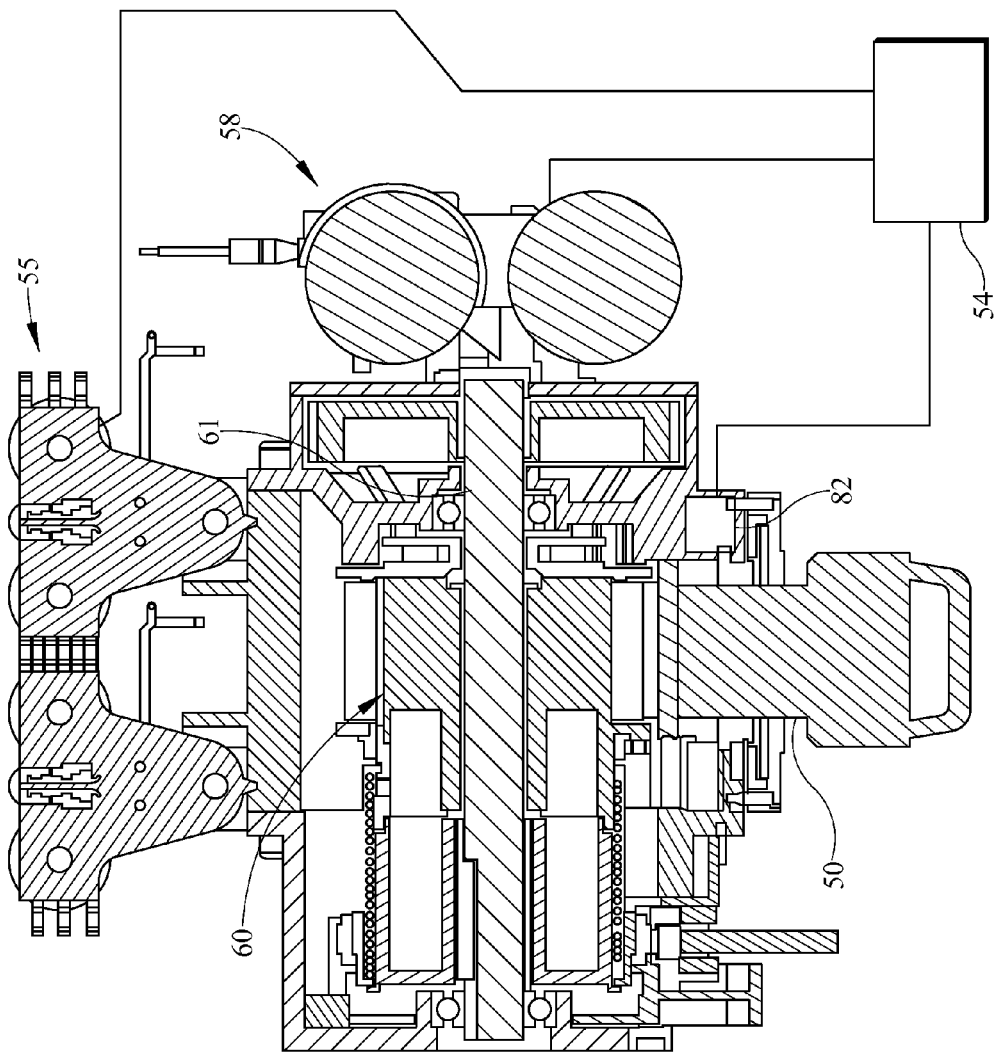
FIG. 6 is a perspective view of the lift system of FIG. 3 showing the lift motor and drum.

The lift assembly 40 includes, a lift 48, a strap 50 configured to be extended and retracted by the lift 48, a sling bar 52 coupled to an end of the strap 50, a sling 53, and a control system 54 as shown in FIG. 3. The lift 48 includes a carriage 55 configured to engage the track 42 of the rail 38 and move the lift assembly 40 along the rail 38, a housing 56 coupled to the carriage 55, motor 58 positioned in the housing 56, and a drum 60 coupled to the shaft 61 of the motor 58 and configured to raise and lower the strap 50 as the motor 58 rotates the drum 60 as shown in FIG. 5. In one contemplated embodiment, the carriage 55 includes a conductor (not shown) configured to electrically couple with the conductor 46 on the rail 38. The sling bar 52 is coupled to the end of the strap 50 and includes aims 52 with sling coupling portions 64 at the ends of the arms 52. The sling coupling portions 64 are configured to receive and removably retain a portion of the sling 53. The sling coupling portions 64 include a retaining element 66 that is configured to prevent the sling 53 from disengaging the coupling portions 64.

Figure 7:
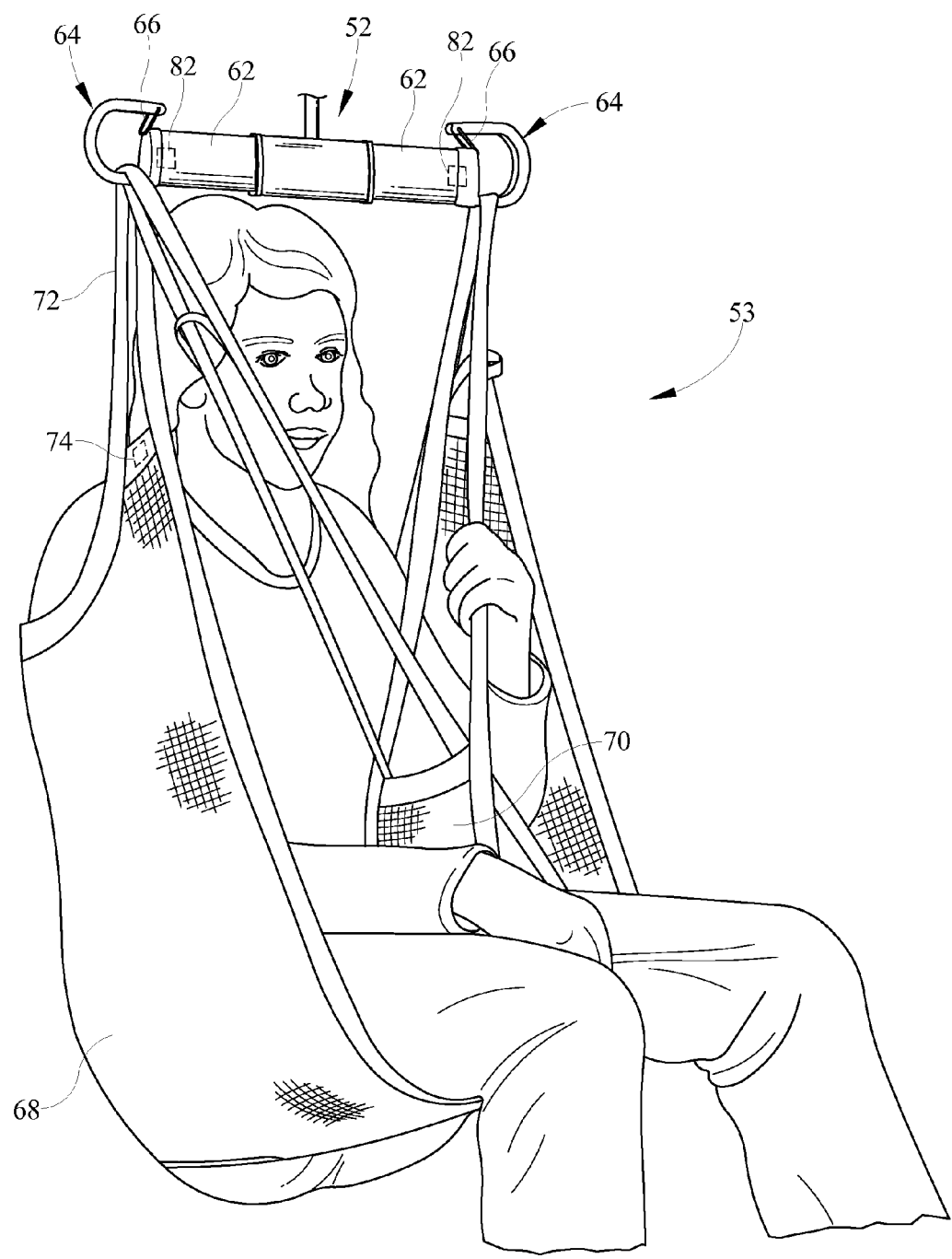
FIG. 7 is a perspective view of a sling configured to be coupled to the sling bar of FIG. 3.

The sling 53 is used to support the person being moved by the lift assembly 48 and includes a main body portion 68, leg portions 70, and connecting straps 72. In one contemplated embodiment, the sling 53 can be one of the slings sold by Liko, such as, the Solo HighBack model 25 sling as shown in FIG. 7. In some contemplated embodiments, the sling 53 includes an RFID tag 74 coupled to the sling 53 that includes information related to the sling, such as, the sling model number, the manufacturing date, the size, the serial number, the date the sling was last inspected, the performance characteristics of the sling, the patient's ID that the sling has been assigned to, and other related information. In one contemplated embodiment, the RFID tag 74 is positioned between the layers of material adjacent to the connecting straps 72. In some contemplated embodiments, the RFID tag 74 can be replaced with a magnet (not shown).

The control system 54 includes a user interface 76, a controller 78, a communication device 80, sensing elements 82, and a battery 83. The user interface 76 includes a pendant 84 with a display 86 and buttons 88 thereon. The buttons 88 provide input to the controller 78 indicative of a user's desire to raise and lower the sling 53, and the display 86 is configured to display information related to the lift system 12, the patient, the room, the facility, and other information. In some contemplated embodiments, the pendant 84 includes an accelerometer 82 that is configured to determine when the pendant's 84 orientation has changed such that the button 88 that causes the lift 48 to lift the person up is pointing downward, and re-assign the button function to the button 88 that is currently pointing upward, so that when a user presses the button 88 that appears to make the lift 48 lift the person, the lift 48 will lift the person (instead of lower). In some contemplated embodiments, the battery 83 is charged via the pendant 84 when the pendant 84 is docked in a docking station (not shown). In another contemplated embodiment, the battery 83 is charged via the conductor 46 on the rail 38. In other contemplated embodiments, the battery 83 is recharged over an Ethernet connection or over a communication bus (i.e., the High Speed DC-CANTM power-line modem transceiver sold by Yamar Electronics).

The sensing elements 82 are configured to sense various operational characteristics of the lift assembly 40 and provide an input signal to the controller 78. In some contemplated embodiments, the controller 78 uses information sensed by the sensing element 82 to determine at least one of the following: the accumulated "drive time" (i.e., in seconds), the amount of weight lifted by the lift system 12 to date (which can be combined with the total weight lifted by other lifting devices 12 on the same wing of the care facility to show the total weight lifted over the entire wing of the care facility), the "drive time" since the device was last serviced (i.e., in days), the accumulated "capacity consumption" for the up/down driver motor (i.e., in amps), the number of resets of a service indicator, the number of accumulated activation of upper current limiting circuit, the number of started and completed and not completed charging cycles, the number of activations of the upper and lower end limit switches, the number of completed lift cycles, the battery level, the number of times the device was overloaded, the percent of the load carried by the patient or the lift, the increase in strength of the patient over time, the patient's weight history, the decrease in assistance of the lift over time, and the number of lift events (compliant lifts and non-compliant lifts).

The sensing elements 82 can be one or more of a variety of sensing devices. In one contemplated embodiment, the sensing elements 82 include an accelerometer positioned within the sling bar 52 that is configured to sense when the sling bar 52 is tilted to one side, which may indicate that the sling 53 is improperly connected to the sling bar 52. In this embodiment, upon detecting the tilted sling bar 52, the lifting motion can be stopped and the user can be alerted about the condition and asked to check the connection of the sling 53 and the sling bar 52 before lifting can resume. In some contemplated embodiments, the sensing element 82 includes a force sensor that is used to measure the weight of the patient being supported by the lift system 12. In some embodiments, the sensing element 82 includes an energy sensor (i.e., an electric current sensor) that is configured to sense the amount of energy being used by the lift system 12 to lift the patient and/or the amount of charge left on the battery 83.

In another contemplated embodiment, the sensing element 82 includes an optical strap scanner that is configured to assess the condition of the strap 50. In some contemplated embodiments, different wavelengths of light can be used to scan the strap 50. In some contemplated embodiments, the optical strap scanner is the c2060 seat belt inspection system sold by FibreScan. In some contemplated embodiments, the optical strap scanner (or other optical sensing device as discussed further below) can be used to sense the distance a person is moved by the lift system 12. In one contemplated embodiment, the optical strap scanner can measure the distance using marks on the strap 50 that are spaced apart a predetermined distance. In one contemplated embodiment, a line on the strap 50 at predetermined intervals can be used. In some contemplated embodiments, patterns can be shown on the strap and can be used to determine if the strap 50 was moving up or down. In one contemplated embodiment, a repeating pattern of three lines of varying length and/or thickness can be used. In another contemplated embodiment, a gray scale coding pattern can be used to, when sensed by the optical strap scanner, determine the distance, speed, and direction the strap 50 has moved.

In another contemplated embodiment, the sensing elements 82 are configured to sense when a sling 53 is connected to the sling bar 52. In one contemplated embodiment, the sensing element 82 a hall-effect sensor that is configured to sense when a sling strap 72, including a magnet coupled thereto, is attached to the sling connector 64. In another contemplated embodiment, the sensing element 82 is a switch that is coupled to the retaining element 66 and is configured to sense when the retaining element 66 is opened and closed, which could signify the sling strap 72 being attached to the sling connector 64. In another contemplated embodiment, the sensing element 82 is an optical sensor that is coupled to the sling connector 64 and is configured to sense when the sling strap 72 is positioned in the sling connector 64. In situations where it is determined that the sling 53 is not properly coupled to the sling bar 52, the user can be alerted and the lift 48 can cease movement of the strap 50 until the user ensures that the sling 53 is properly coupled to the sling bar 52.

In another contemplated embodiment, the sensing element 82 includes a RFID reader coupled to the sling bar 52 and configured to read RFID tags coupled to equipment within a predetermined distance of the sling bar 52. In one contemplated embodiment, the RFID reader can sense when a sling 53 is positioned within a predetermined distance of the sling bar 52 and can be indicative of the sling 53 being attached to the sling bar 52. In some contemplated embodiments, sensing that the sling 53 is near the sling bar 52 in combination with sensing that a sling bar is supporting a weight is indicative of the sling 53 being attached to the sling bar 52. In some contemplated embodiments, multiple RFID readers can be used to triangulate the location of the different RFID tags 74 to see if a sling 53 is coupled to the sling bar 52. In some contemplated embodiments, the RFID reader can alert a user as to when an unknown or unapproved sling 53 is being used with the lift system 12. For example, if the incorrect size or weight rated sling 53 is being used with the patient, the system can alert the user. In another example, if the sling 53 is not assigned to the person, the user can be alerted. In some contemplated embodiments, the system can also inform the user which model sling 53 would be appropriate for them to use with the patient. In some contemplated embodiments, the system can alert the user as to the condition of the sling 53. In other contemplated embodiments, the RFID reader can also write to the RFID tags to store performance information, association information, or other information about the caregiver, patient, facility, sling condition/status, or other information.

In some contemplated embodiments, the controller 78 can use the RFID reader to associate the person support system 14, the sling 53, the patient, the caregiver, and other devices adjacent to the RFID reader. In one contemplated embodiment, the RFID reader is coupled to the sling bar 52 and is configured to read any RFID tags within a predetermined distance, i.e., three feet, from the reader and store in memory, or write to the RFID tags, what devices are being used together to associate them with one another. In some contemplated embodiments, the RFID reader can be used to associate equipment (i.e., a lift and/or a sling 53) and people (i.e., a caregiver and/or a patient) with one another and the room if they have RFID tags and are in the vicinity of the RFID reader. In some contemplated embodiments, other equipment in the room, the person support system 14, medications, and other devices including RFID tags can be associated with one another when they are in the vicinity of the RFID reader.

Figure 8:
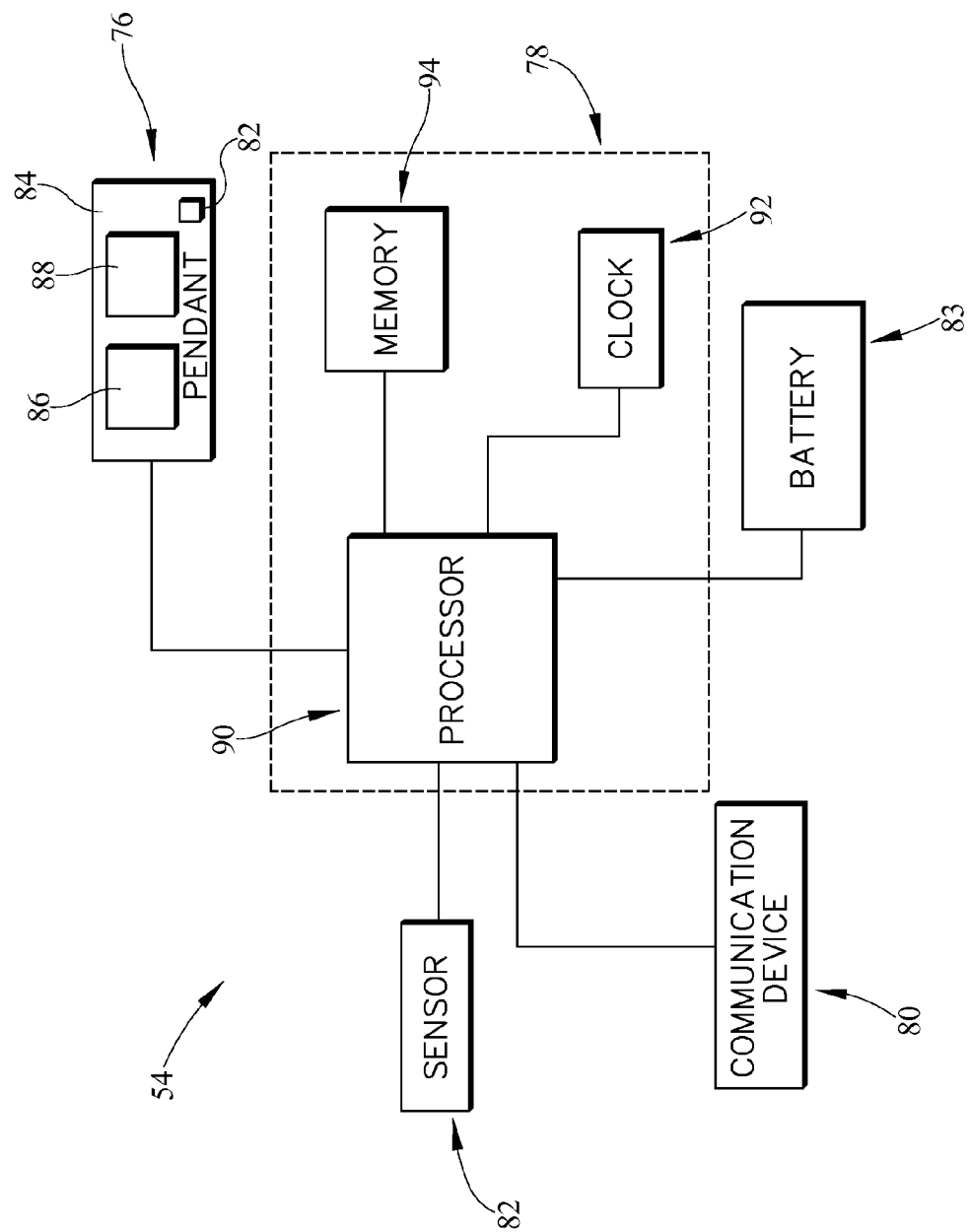
FIG. 8 is a diagrammatic view of a control system of the overhead lift of FIG. 3.

The controller 78 is configured to receive inputs from the user interface 76 and the sensing elements 82 and control the operation of the lift 48 as a function of the input. The controller 78 includes a processor 90, a clock 92, and memory 94 as shown in FIG. 8. In some contemplated embodiments, the clock 92 is removed and date and/or time information is provided by the information management system 18 or through the hospital network 20. The processor 90 is electrically coupled to memory 94, the battery 83, the clock 92, the sensing elements 82, the communication device 80, and the user interface 76. The processor 90 is configured to execute instructions stored in memory 94. In some contemplated embodiments, the instructions define procedures that cause the processor 90 to collect and process information sensed by the sensing elements 82 that is related to the lift system 12 or the patient being moved by the lift system 12 or the person support system 14 or the care facility or other equipment in the vicinity of the lift 48.

Figure 9:
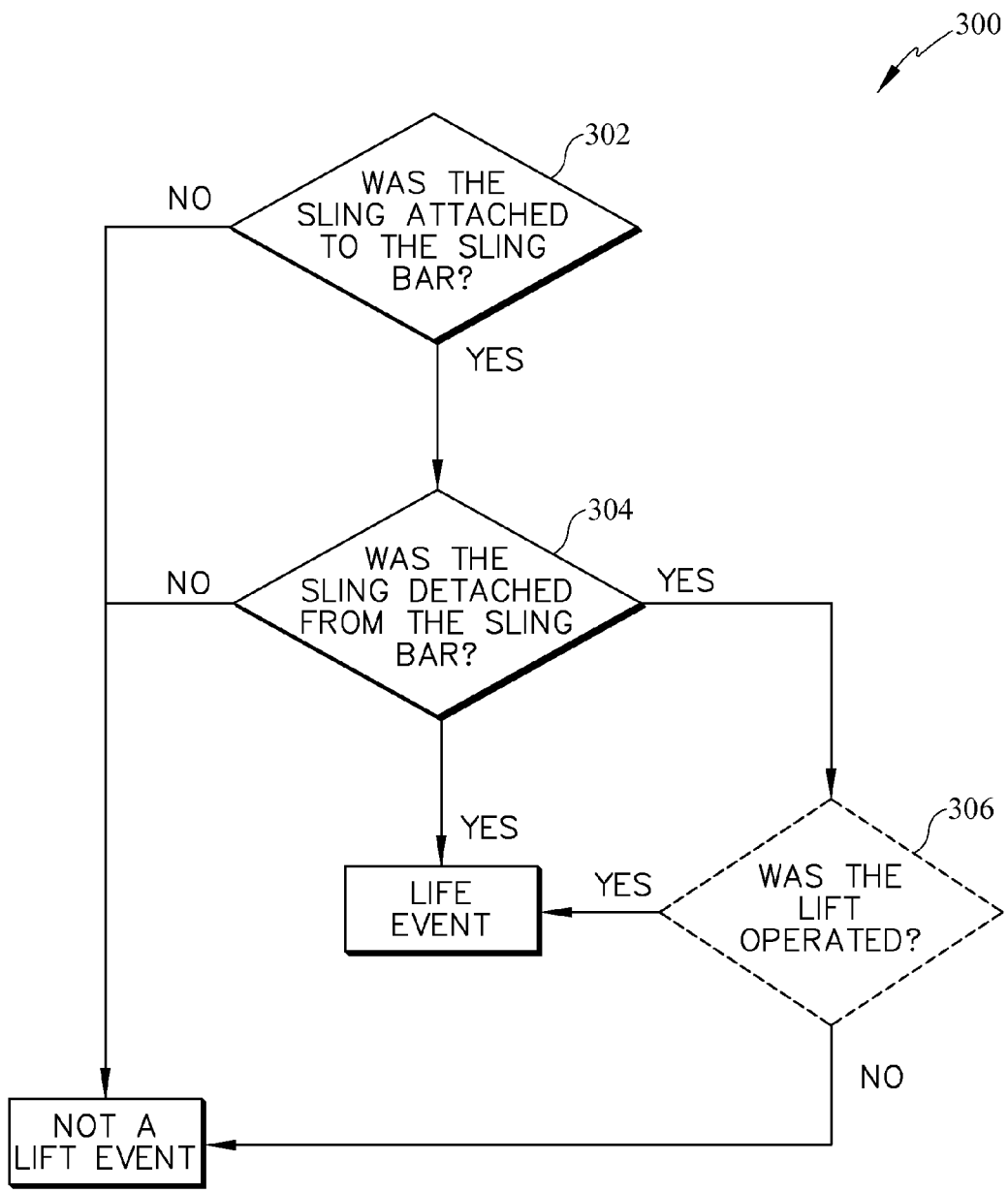
FIG. 9 is a flow chart for a procedure for determining when a lift event has occurred.

In one contemplated embodiment, the instructions define a procedure 300 that determines when a lift event has occurred as shown in FIG. 9. Procedure 300 begins with step 302 where the processor 90 receives a signal from a sensing element 82 indicative of a sling 53 being coupled to the sling bar 52. In one contemplated embodiment, a sensing element 82 is coupled to the sling bar 52 and is configured to sense when the retaining element 66 is moved to allow the sling 53 to be attached to the sling bar 52. In one contemplated embodiment, the sensing element 82 is a contact sensor that is in a first state when the retaining element 66 is closed (as shown in FIG. 9) and in a second state when the retaining element 66 is opened to allow the sling straps 72 to be coupled to the sling bar 52. In some contemplated embodiments, a mechanical switch, hall-effect sensor, optical sensor, RFID reader, magnetic sensor, or force sensor (sense weight) can be used to determine the state of the retaining element 66 or the engagement of the sling straps 72 with the sling connector 64. In some contemplated embodiments, the sling 53 includes RFID tags 74 and/or magnets coupled thereto as previously discussed.

In step 304, the processor 90 receives a signal from the sensing element 82 when the sling 53 is uncoupled from the sling bar 52. In one contemplated embodiment, the sensing element 82 indicates that the retaining element 66 was moved a second time. Upon determining that the retaining element 66 has been opened twice, the processor 90 indicates that a lift event has occurred and stores information related to the lift event, including the time, in the memory 94.

In some contemplated embodiments, a lift event has not occurred unless steps 302 and 304 are true and an operational characteristic of the lift 12 has been sensed in step 306. In one contemplated embodiment the operational characteristics include, but are not limited to, the distance the person has been moved, the weight of the person supported on the lift 12, the amount of time the lift 12 was being used, the amount of current used to power the lift motor 58, and the duration the buttons 88 on the pendant 84 were pressed and held. The distance the person is being moved can be determined using a potentiometer configured to rotate as the strap 26 is extended and retracted. The distance the person is being moved can also be determined using an optical sensor coupled to the lift housing 56 and configured to sense patterns on the strap 50 as the strap 50 moves past the sensor. In one contemplated embodiment, the pattern includes three indicators (such as, 3 horizontal lines of increasing length on the flat side of the strap 50) that repeat along the length of the strap 50. Using patterns of indicators enables the processor 90 to determine the direction, distance, and speed the strap 50 is moving. In some contemplated embodiments, a single indicator spaced apart at predetermined intervals is used to indicate the distance traveled. In some contemplated embodiments, the strap inspection system checks the condition of the strap 50 and senses the distance the strap 50 has traveled. In some contemplated embodiments gray scale coding can be used to determine the distance, the direction, and the speed at which the person was moved. In some contemplated embodiments, the gray scale coding can be located on the motor shaft 61 or edge of the strap 50 and an optical sensor can be used to read the code. In other contemplated embodiments, the marks can be on the edges of the strap 50.

In another contemplated embodiment, step 306 includes sensing when other devices having RFID tags on them are proximate to the lift bar 52. Generally, when in storage, the strap 50 and the sling bar 52 are retracted. In this position, an RFID reader coupled to the sling bar 52 and configured to read RFID tagged objects within 3 feet of the reader would generally not be in communication with any RFID tags. When the lift 12 is being used, the sling bar 52 is lowered and brought to a location where the RFID tag 74 on the sling 53 and the caregiver's badge and/or the person support system 14 can be read. In some contemplated embodiments, the RFID reader can associate objects having a RFID tag within the 3 foot radius of the RFID reader. In one example, the RFID reader can associate a sling 53 including an RFID tag with a caregiver and a person support system 14 within a predetermined distance from the reader. The RFID tags on the sling 53 can include information about the sling model number, performance characteristics of the sling (i.e., max load is 500 lbs), size of the sling 53, and other characteristics of the sling 53.

Figure 10:
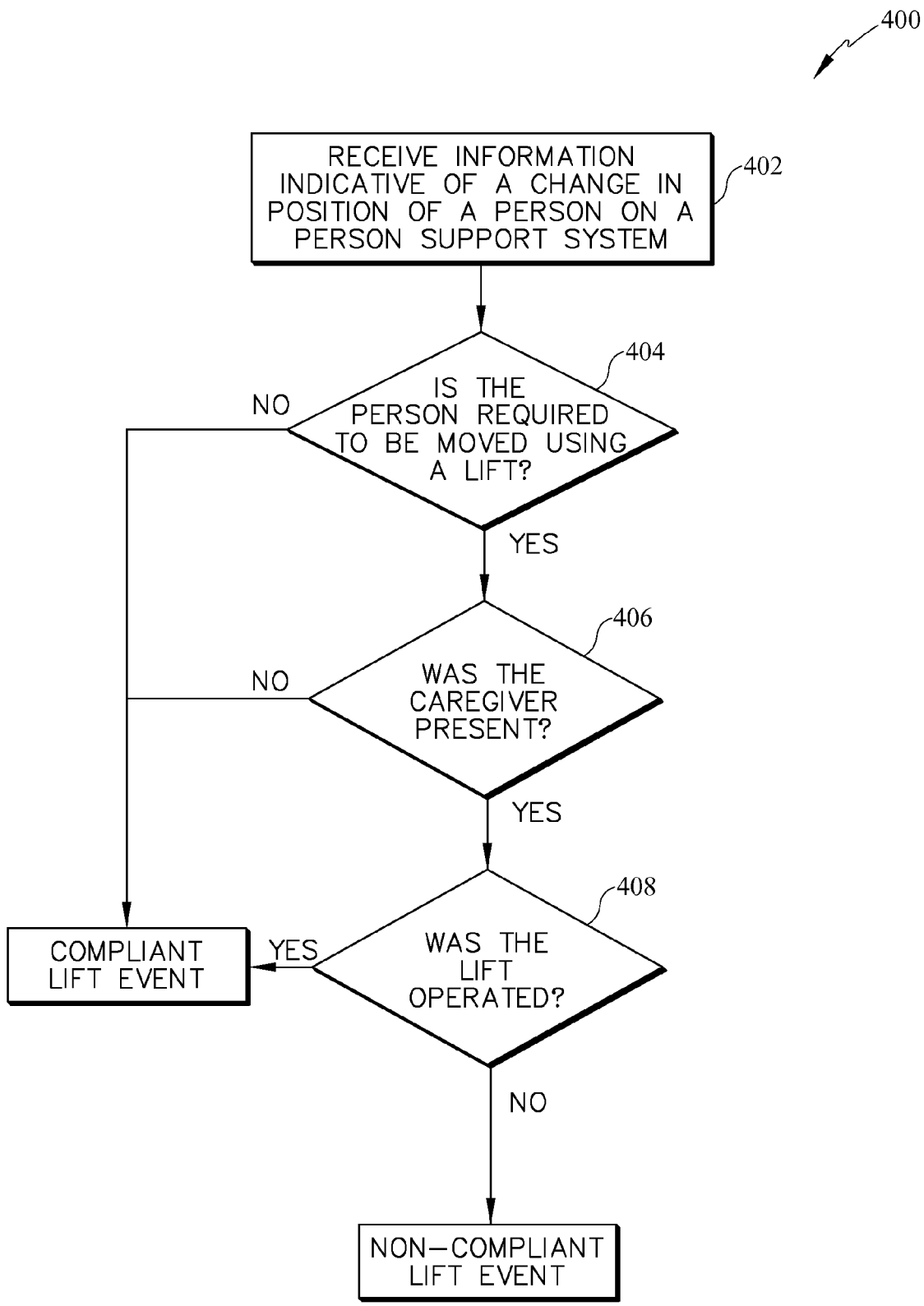
FIG. 10 is a flow chart for a procedure for determining when non-compliant lift was performed, such as, when a person is moved on a person support system and a lift was not used, but should have been.

In one contemplated embodiment, the instructions define a procedure 400 that determines when a lift should have been used, but was not used to move a patient as shown in FIG. 10. Procedure 400 can be executed on the person support system 14, the lift system 12, or on a remote system, including the information management system 18. Procedure 400 begins with step 402 in which the processor 90 receives information from the person support system 14 indicative of a change in position of a person supported on the person support system 14. In one contemplated embodiment, the change in position can be detected based on a change in the person's center of gravity exceeding a predetermined threshold. In another contemplated embodiment, the change in position can be detected using a pressure sensing mat positioned on the mattress 30 (or using pressure distribution in bladders in an active mattress 30) and measuring the difference between an initial pressure profile and a new pressure profile.

In step 404, the processor 90 receives information from the EMR system indicative of whether the person is required by the hospital's protocol to be moved using a lift. If the person is, the processor proceeds to step 406.

In step 406, the processor 90 receives a signal indicative of whether a caregiver was present when the movement occurred. In one contemplated embodiment, the location of the caregiver at the time of the movement can be provided by an asset locating and tracking system. In one contemplated embodiment, the location of the caregiver at the time of the movement can be determined by the RFID reader 82 coupled to the sling bar 53. If the RFID reader coupled to the sling bar does not sense the RFID tag in the caregiver's badge at about the time the movement occurred, the indication may be that the caregiver was not present at the time. If the processor determines that a caregiver was present, the processor proceeds to step 408.

In step 408, the processor 90 receives a signal indicative of whether or not the lift system 12 was used at the time the movement occurred. Any of the operational characteristics previously mentioned can be used to determine whether the lift system 12 was operated. If the lift system 12 was activated, the processor 90 indicates that the lift event complied with the care facility's lift protocol. If the lift system 12 was not activated, the processor 90 indicates that the lift event did not comply with the care facility's protocol.

Figure 11:
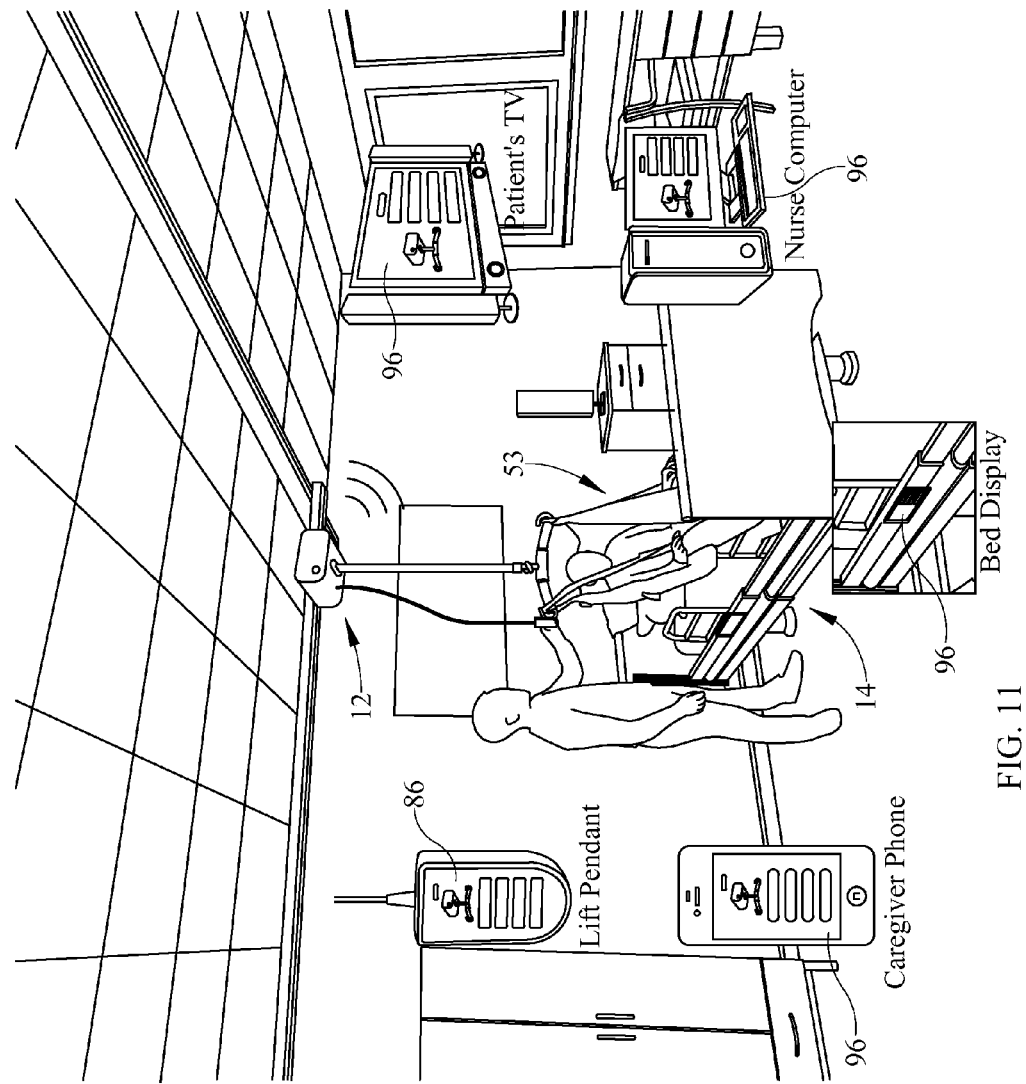
FIG. 11 is side perspective view of a caregiver lifting a person off the person support system with the person lift and the lift communicating with various remote devices to display information about the lift and/or patient according to one illustrative embodiment of the disclosure.
Figure 12:
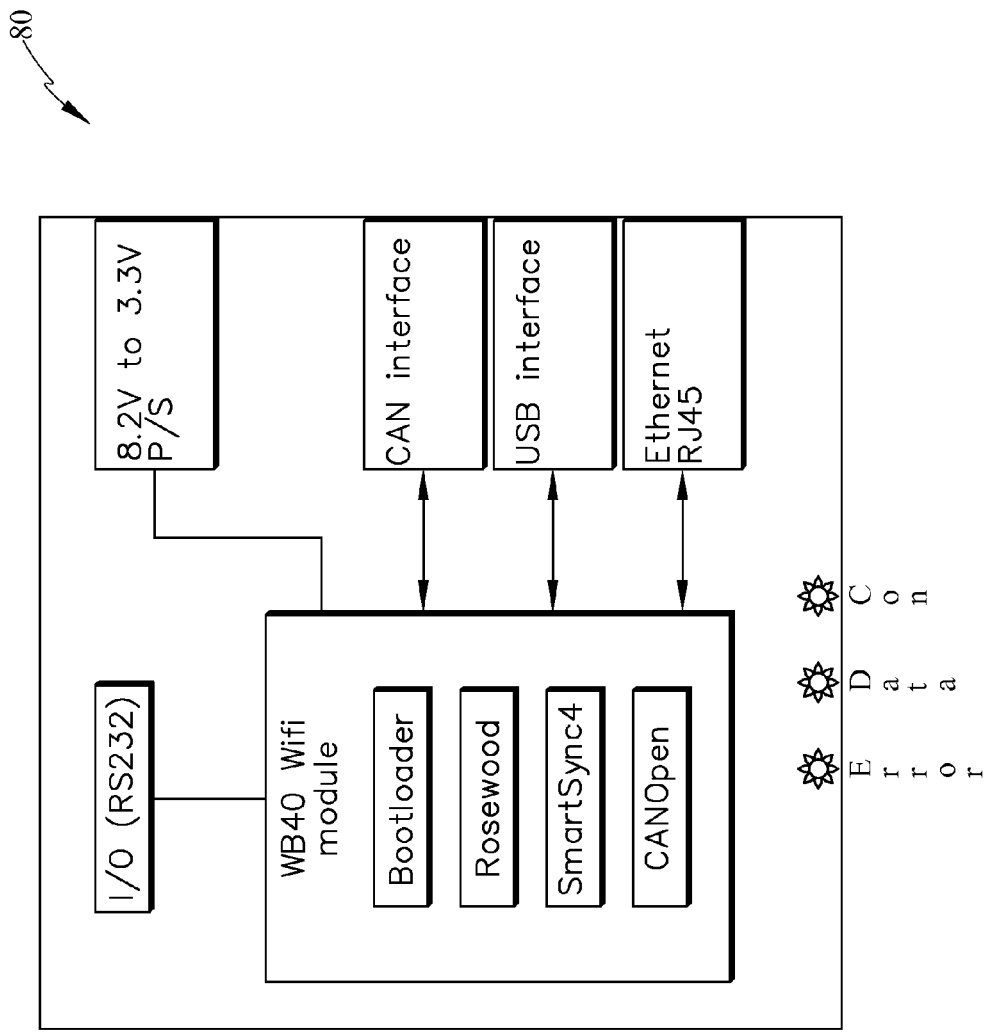
FIG. 12 is a diagrammatic view of the communication device of the lift system of FIG. 3 according to one illustrative embodiment.
Figure 13:
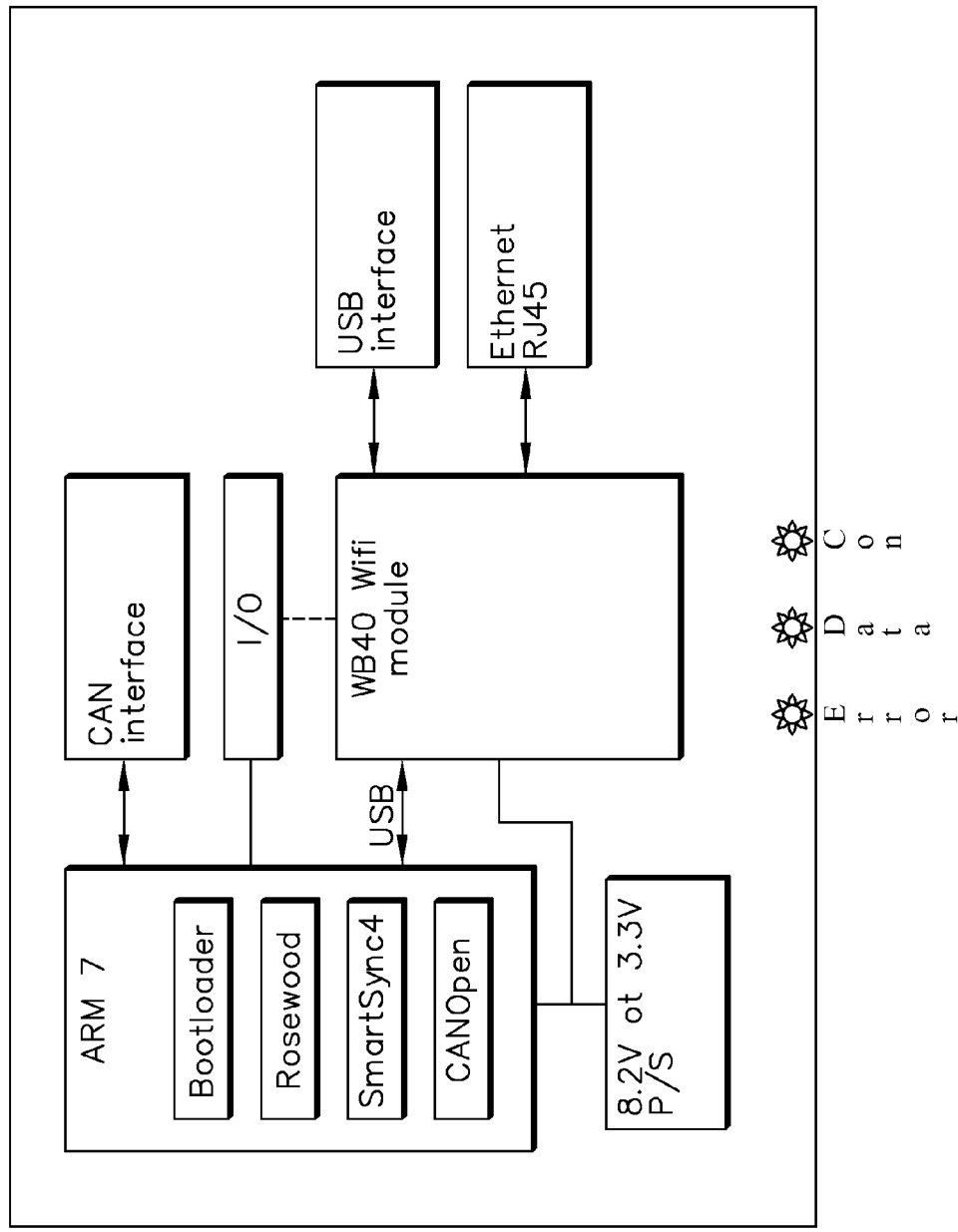
FIG. 13 is a diagrammatic view of the communication device of the lift system of FIG. 3 according to another illustrative embodiment.
Figure 14:
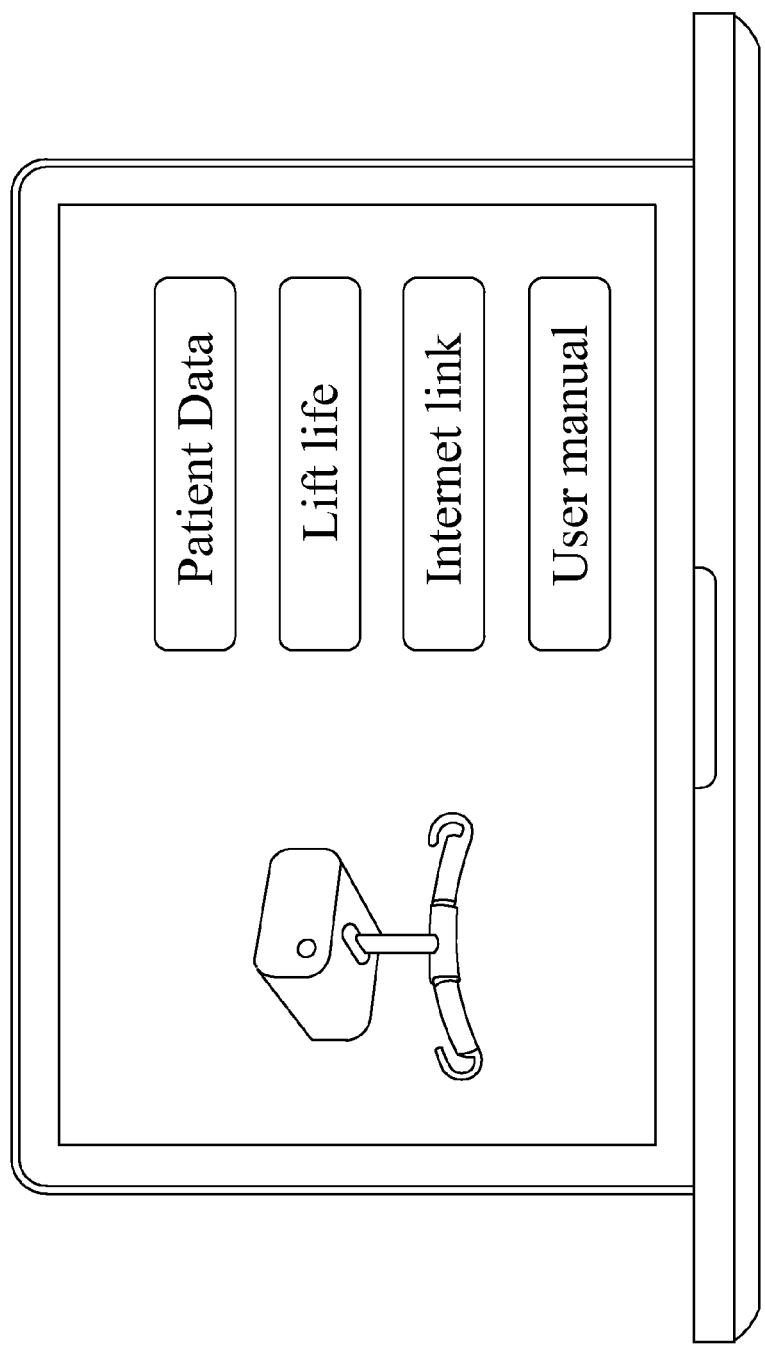
FIG. 14 is a screen shot of the interface displaying a menu including options where a user is able to receive information related to the patient (patient data) or the lift (lift life), links to locations on the internet (internet links), and product instruction materials (user manuals) according to one illustrative embodiment of the disclosure.

The communication device 80, as shown in FIGS. 12 and 13, is configured to communicate information about the lift 12 and the patient associated with the lift to a plurality of locations and/or devices as shown in FIG. 11. In one contemplated embodiment, the communication device 80 communicates information that is charted in an electronic medical record (EMR). In one contemplated embodiment, the communication device 80 is a radio frequency transceiver. In other contemplated embodiments, the communication device 80 can be configured to communicate with the information management system 18 through a fiber-optic cable, over a power connection (i.e., where power is communicated to the lift system 12 via the rail 38 as shown in FIGS. 5 and 14 and), over a LIN Bus, via Bluetooth or Wi-Fi or NFC (near field communication) or other wired or wireless communication methods. In one contemplated embodiment, the devices and locations the information is communicated to includes the pendant 84, a caregiver's mobile device (i.e., cell phone or tablet computer or the like), control panels on the hospital beds 14 (i.e., beds associated with the lift system 12), a computer terminal at a nurse station, and/or a television in the patient's room. The communication device 80 includes a wifi module (i.e., WB40 wifi module sold by Laird Technologies) that can have various programs loaded onto it and can send and receive signals on various types of communication platforms, including CAN, USB, RJ45, and RS232 as shown in FIG. 12. In some contemplated embodiments, the programs are loaded onto a separate controller and the controller configures the wifi module as shown in FIG. 13.

Figure 15:
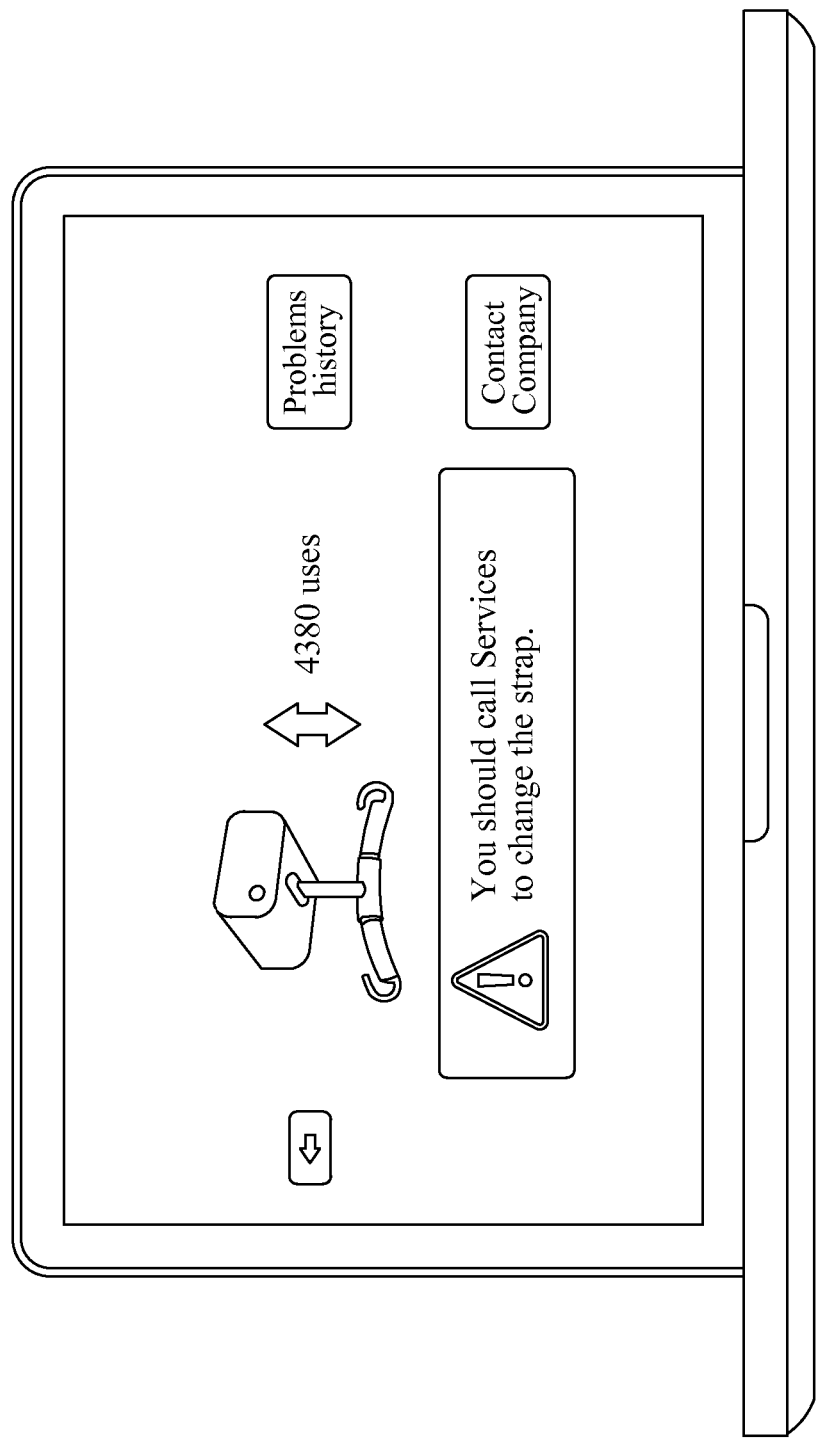
FIG. 15 is a screen shot of the interface displaying a second menu after the lift life menu option has been chosen, which includes information related to the number of times the lift was used, past errors, manufacturer contact information, and maintenance suggestions.
Figure 16:
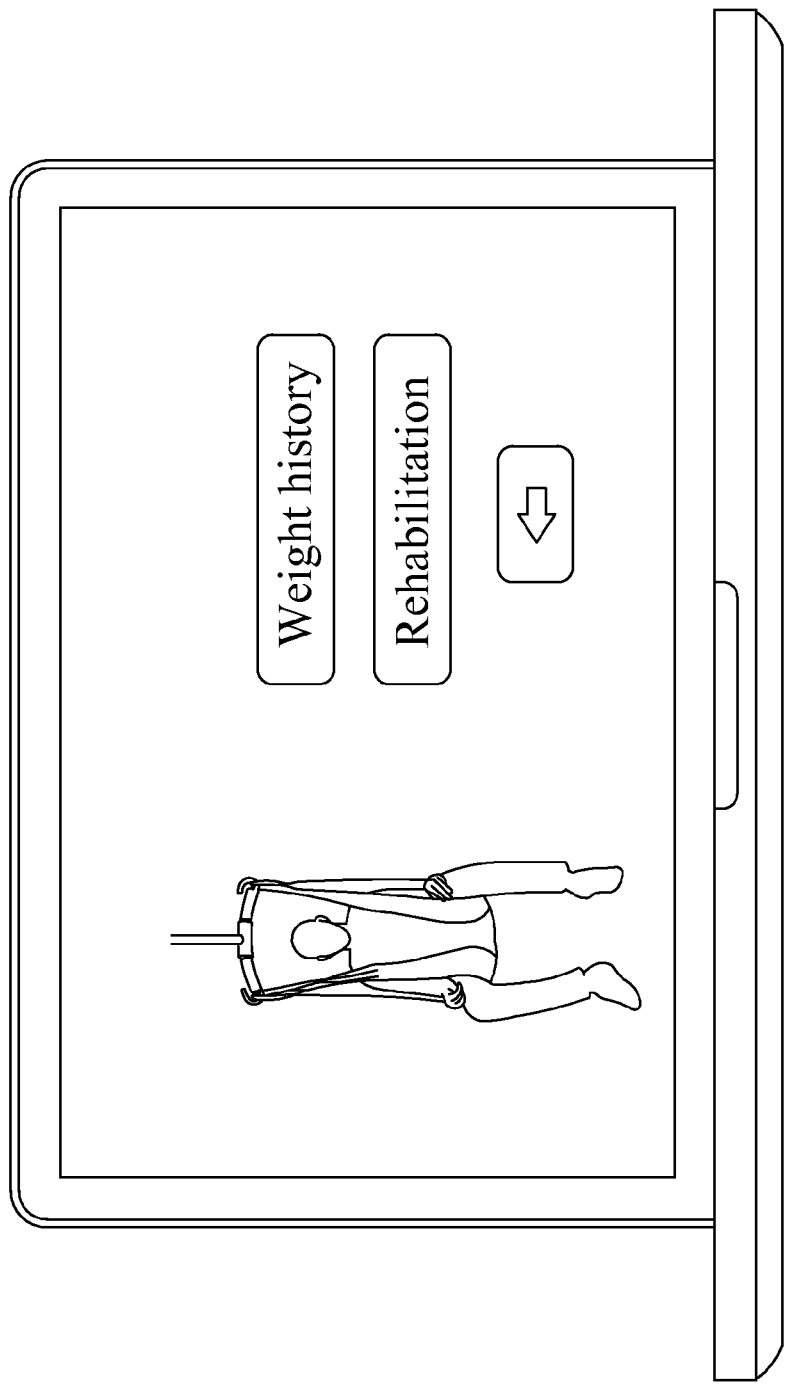
FIG. 16 is a screen shot of the interface displaying a third menu after the patient data menu option has been chosen, which includes information related to weight history and rehabilitation according to one illustrative embodiment of the disclosure.
Figure 17:
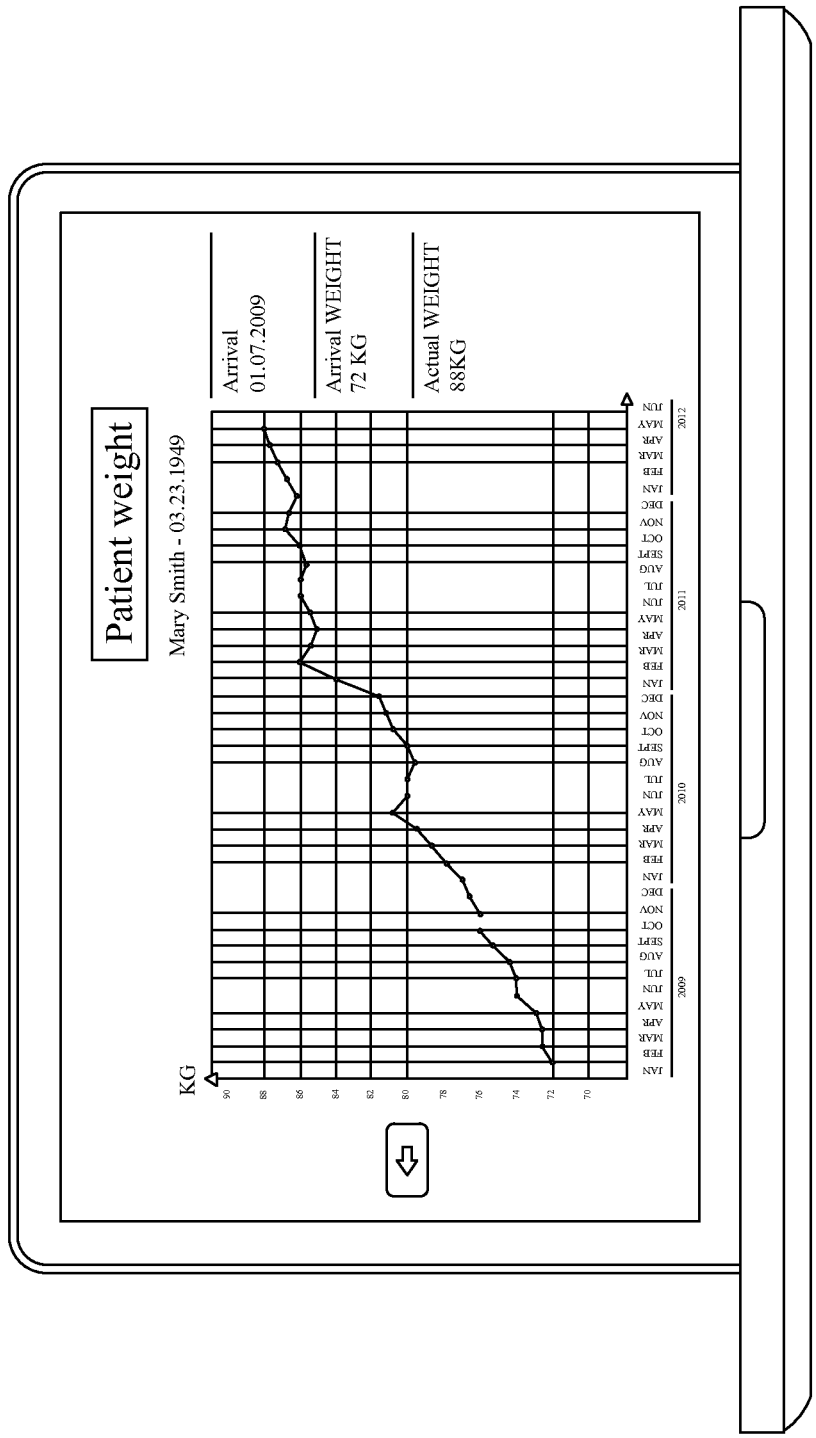
FIG. 17 is a screen shot of the interface displaying the patient's weight history according to one illustrative embodiment of the disclosure.
Figure 18:
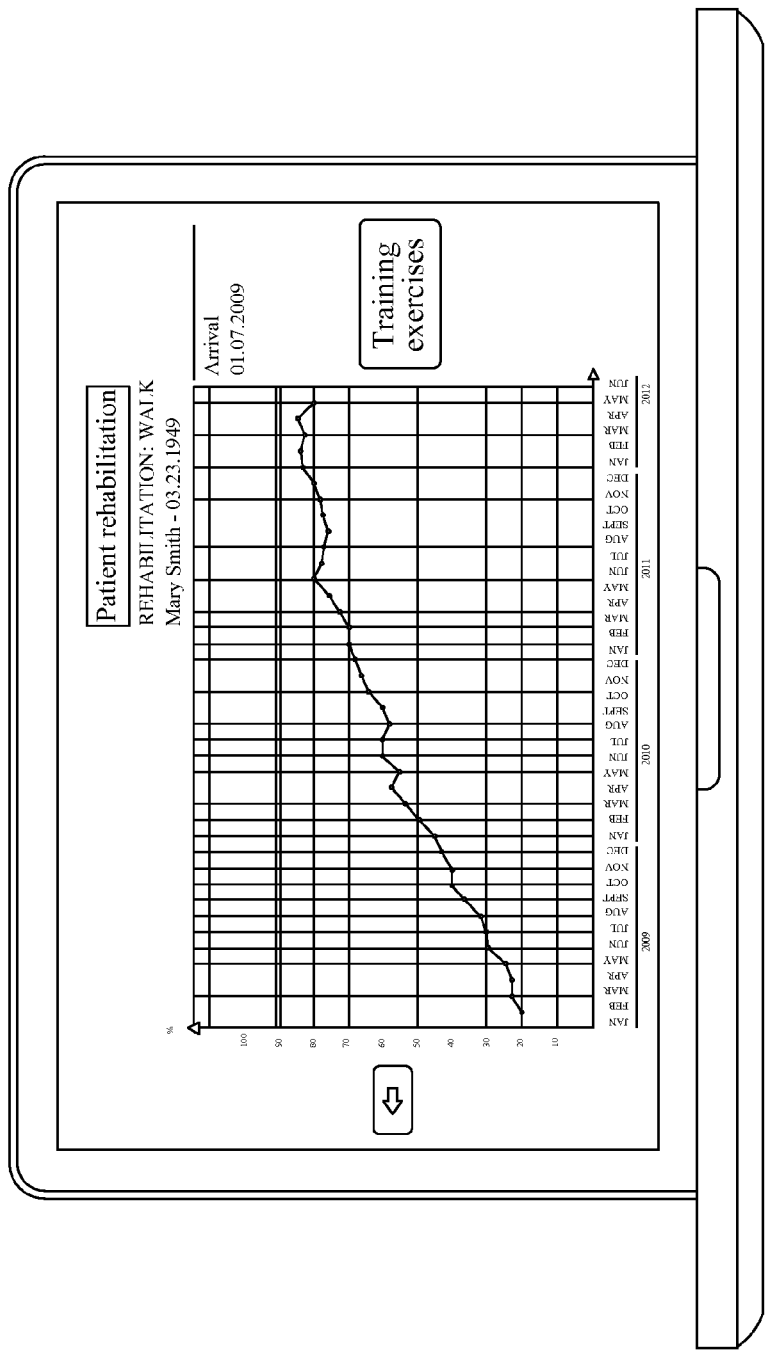
FIG. 18 is a screen shot of the interface displaying the patient's rehabilitation history according to one illustrative embodiment of the disclosure.

The devices and locations may have a display 96 or graphical user interface 96 (including the pendant display 86) that is configured to show the information being communicated by the lift system 12. In some contemplated embodiments, the display 44 includes a touch sensitive display. In some contemplated embodiments, the information being displayed is also communicated from an electronic medical record (EMR), the information management system 18, the hospital network 20, or other information sources. The information can be displayed a number of ways on the displays 44. In one contemplated embodiment, a first screen or home screen is displayed on the display 44 of a computer as shown in FIG. 14. The home screen includes a number of links that enable the user to access information corresponding to the title of the link. In this embodiment, the links enable a user to access information corresponding to the patient (i.e., patient data), the lift system 12 (i.e., lift life), internet links and user manuals. If the patient selects the lift life link, a second screen is displayed that shows a picture of the lift, the number of times the lift has been used, warnings messages or caution messages or tips (i.e., maintenance required for strap—call manufacturer), a link to a listing of errors or problems, and a link to contact information for the manufacturer as shown in FIG. 15. If the patient data link is selected, the display 44 displays a third screen that includes additional links that allow the user to access information corresponding to the patient's weight history and rehabilitation history as shown in FIG. 16. If the patient weight link is selected, a fourth screen appears with a graph showing the patient's weight over time is displayed on the display 44 as shown in FIG. 17. If the rehabilitation history link is selected, fifth screen appears with a graph showing the type of rehabilitation activity being rehabilitated (i.e., walk), the person's progress over time, and a link to a listing of rehabilitation exercises as shown in FIG. 18. Each of the screens includes a back button that will take you to the previous screen.

In one contemplated embodiment, upon admittance to a care facility, a caregiver can determine what equipment will be needed for the patient and utilize the information management system 18 make sure the appropriate equipment gets placed in the patient's room. To determine if a lifting device is necessary, a caregiver may answer a number of questions on a questionnaire, which may be dictated by the care facility's care protocol. In one contemplated embodiment, the questionnaire includes the following questions: is the patient currently using mobility aids in the home, range of motion demonstrations, whether the patient bear weight (if yes, no sling is needed), whether the patient is cooperative (if no, use a full body sling lift and two caregivers), and whether the patient has upper extremity strength (if no, use a full body sling lift and two caregivers, but if yes, use a seated transfer aid). In cases where the patient can bear some weight and they are cooperative, a caregiver can use a stand and pivot technique or powered standing assist lift (if not, they can use a full body sling and two caregivers).

Figure 19:
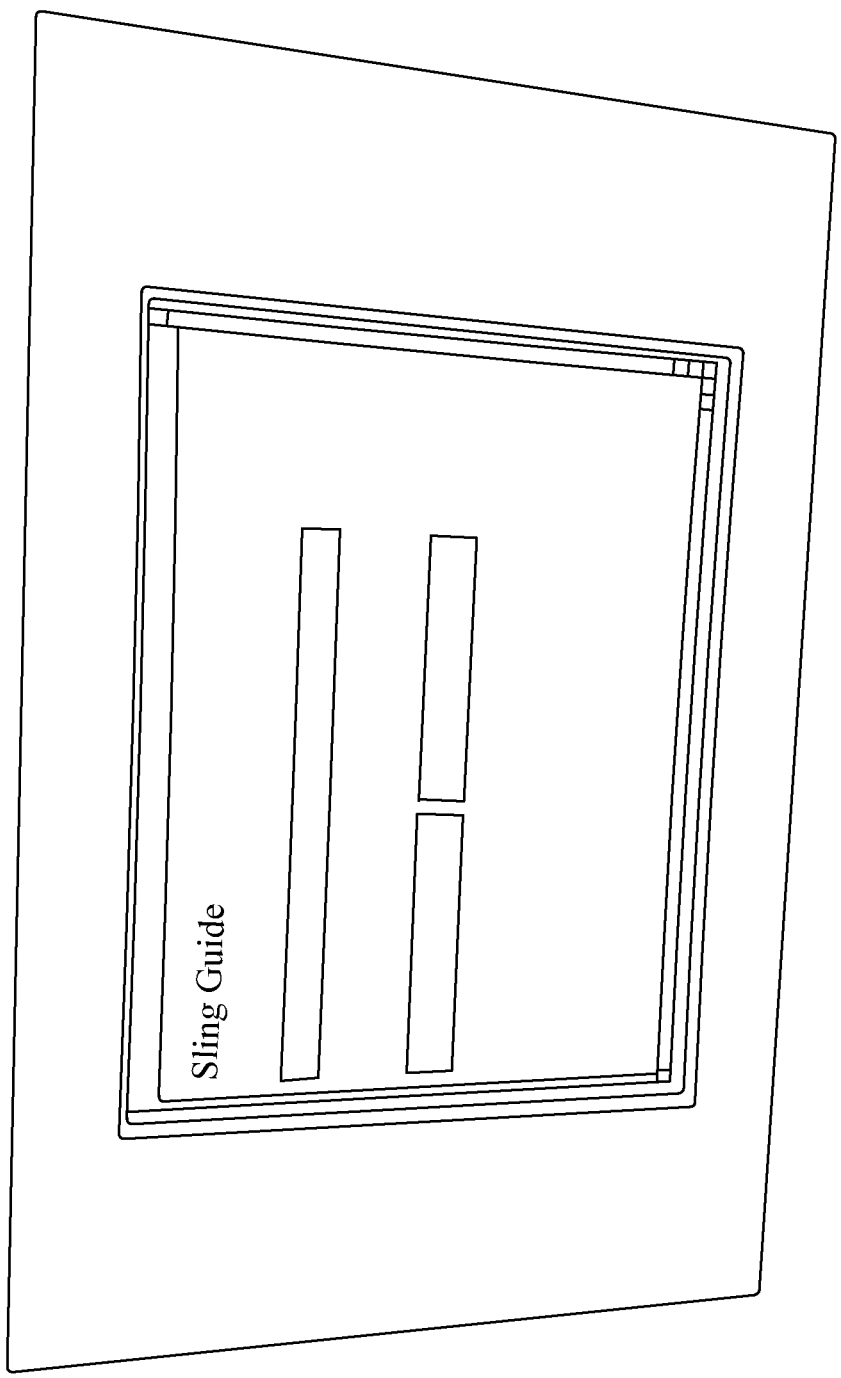
FIG. 19 is a side perspective view of a user interface displaying a guide that can be used to help determine what sling(s) the caregiver can use for the patient.

If the caregiver determines that a lift system 12 is needed for the patient, the caregiver can use an electronic sling guide to help the caregiver pick an appropriate sling 53 or harness. In one contemplated embodiment, the electronic sling guide is displayable on a wall mounted touch screen display, such as the GRS module shown in FIGS. 19-20. In another contemplated embodiments, the sling guide is configured to be pushed to other displays, including mobile device displays (i.e., cell phones, tablet computers, or the like), control panels on hospital beds (i.e., the hospital bed 14 associated with the lift system 12), a computer at the nurse station, a television in the patient's room, and the pendant 84. In one contemplated embodiment, the sling guide is the smart sling guide displayed on Hill-Rom's web site (http://www.hill-rom.com/usa/Products/Category/Patient-Handling/Slings-Lift-sheets/Sling-guide/) and shown in FIG. 19. The sling guide displays a number of options that the caregiver can select to filter a database containing the various types of slings the care facility uses in order to help direct the caregiver to a sling or group of slings that would be most suitable for the patient's needs. In some contemplated embodiments, the options are selected by touch or with an electronic pointing technique (i.e., using a mouse or buttons on a control panel or the control pendant 30). Once the list of slings 53 is filtered, the sling guide can provide the user with the model numbers of the slings 53 and with a location where the slings 53 will likely be found in the care facility (i.e., the room where the sling 53 or the sling storage room). In some contemplated embodiments, slings 53 include RFID tags that allow the sling to be located in the care facility. In some contemplated embodiments, the sling RFID tags are washable. Further training can be provided to show how to properly attach the sling to the patient and connect the selected sling to the lift. The training can be displayed on the television in the patient's room or on a display near the lift.

Figure 20:
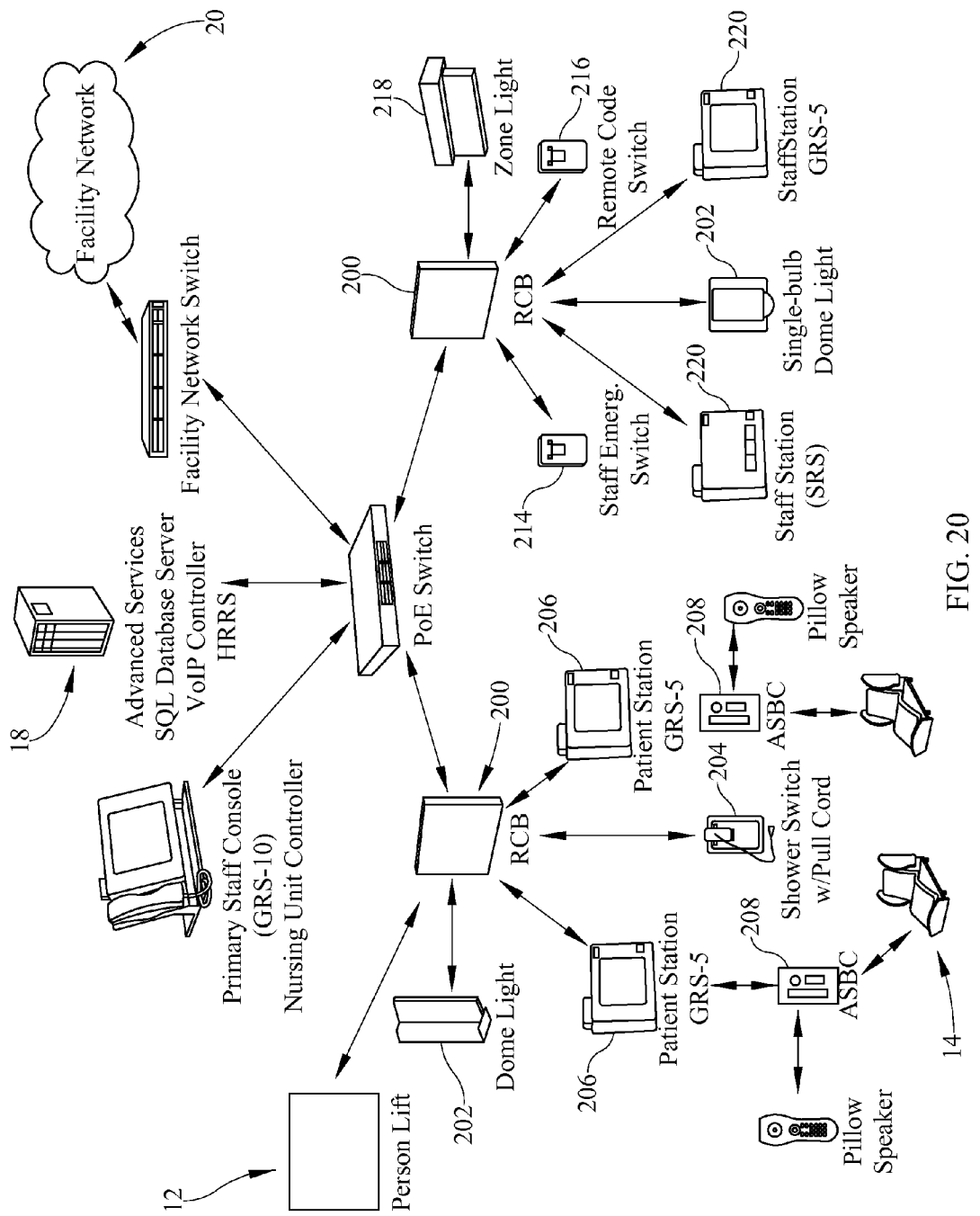
FIG. 20 is a diagrammatic view of the monitoring system of FIG. 1 showing a more detailed view of how the various systems and devices are connected.
Figure 21:
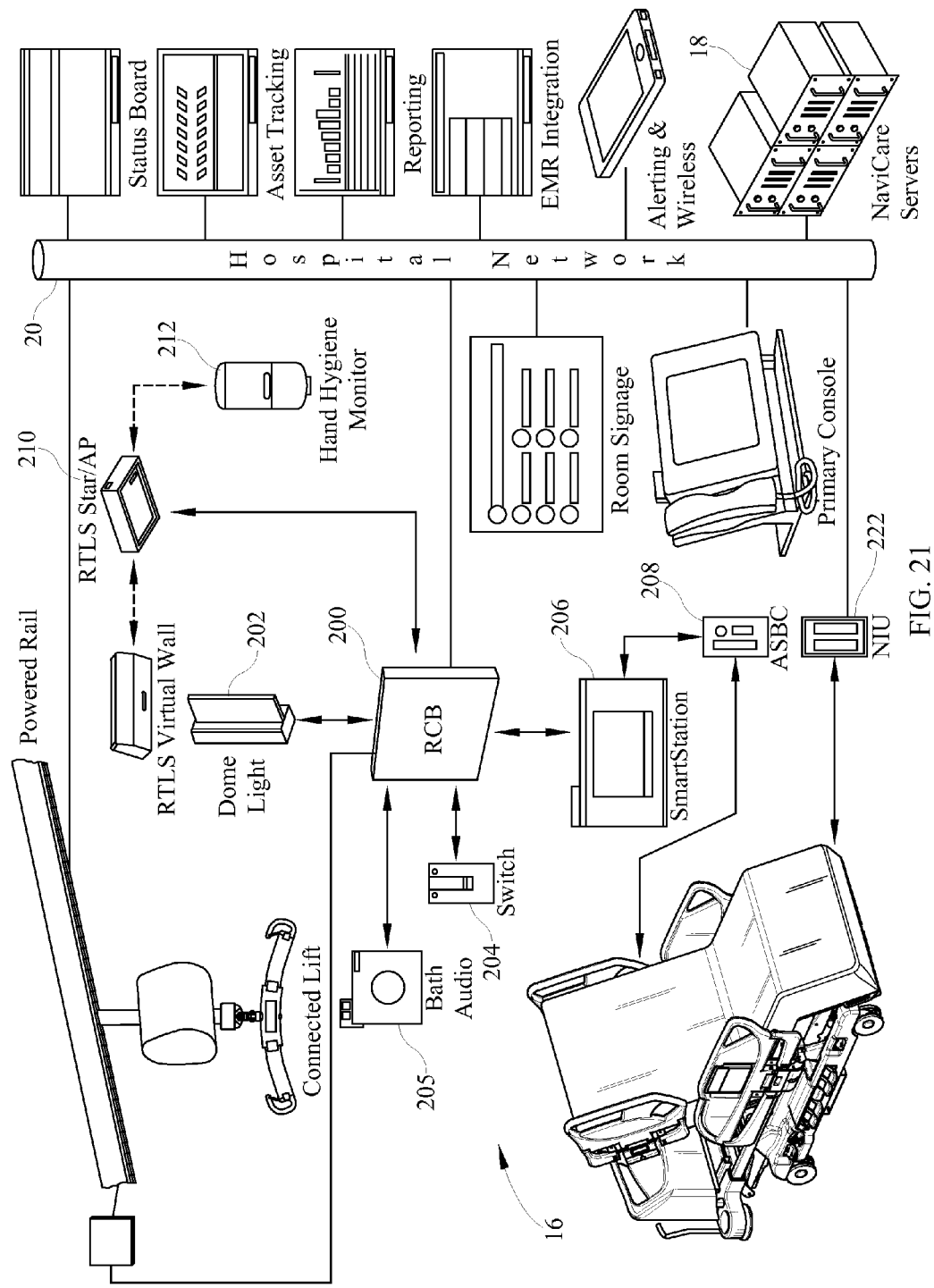
FIG. 21 is a diagrammatic view of the monitoring system of FIG. 1 showing another illustrative embodiment of how the various systems and devices are connected.

As shown in FIGS. 20-21, the communication system 16 includes a room control board 200 that provides communication path between various input/output devices and the information management system 18 and hospital network 20. In one contemplated embodiment, the input/output devices include the lift system 12, which communicates directly with the board 200 via a wired or wireless connection. In another contemplated embodiment, the input/output devices include a dome light 202, a shower pull switch 204, a bathroom intercom 205, a patient room station 206 (such as the Graphical Room Station 5 (GRS-5) sold by Hill-Rom) which can include an Audio Station Bed Connector (ASBC) 208, a real-time locating system (RTLS) 210, a hand-hygiene compliance monitoring system 212, a staff emergency switch 214, a code switch 216, a zone light 218, and staffing stations 220 (such as the Standard Room Stations (SRS) sold by Hill-Rom) as shown in FIG. 20. In some contemplated embodiments, the communication system 16 includes a network interface unit (NIU) 222 that is configured to provide a communication path between the hospital network 20 and the person support system 14 (or other devices connected to the NIU 214) as shown in FIG. 21. In some contemplated embodiments, a power over Ethernet switch (PoE) 224 is positioned between the information management system 18 and the hospital network 20. In some contemplated embodiments, the information management system 18 communicates with the communication system 16 via the hospital network 20 as shown in FIG. 21.

The information management system 18 is configured to route the information it receives from the lift system 12, patient support system 14, and the various other input/output devices over the hospital network 20 to the appropriate destination. In one contemplated embodiment, the information management system 18 includes at least one of a workflow automation feature, a nurse communication feature, a real-time locating feature, a device connectivity feature, and a compliance feature (such as, hand hygiene compliance monitoring). In some contemplated embodiments, the information management system 18 includes a computer server that hosts the NaviCare® platform sold by Hill-Rom.

The information management system 18 is configured to display information related to the care facility, the staff, the care facility's protocols, the patients in the care facility, and the equipment in the care facility, and run reports on various types of information as shown in FIGS. 22-26. In one contemplated embodiment, the information management system 18 displays a first screen or home screen with a summary of information for a unit or wing of a care facility and a number of links that direct the user to screens that display more detailed information corresponding to the title of the link as shown in FIG. 22. The summary on the home screen can include the room number, patient name associated with the room number, a type of protocol selected for the patient (i.e., lift required, falls risk), the primary caregiver's name, the status of the bed exit detection system, the status of the siderails on the hospital bed 14, the height of the upper deck of the hospital bed 14, the status of the brake system on the hospital bed 14, the angle of inclination of the head of bed section of the deck, the amount of charge remaining on the lift battery, the daily amount of lift events, and whether or not a lift emergency is occurring (i.e., whether or not someone pushed/pulled on the emergency button/strap that shuts down the lift). In some contemplated embodiments, the summary can also include, among other things, a patient lift assessment score (i.e., whether or not the person needs a lift), the total weight lifted and/or the total lift events per day by the lift, by all the lifts in a wing or unit, or all the lifts in the care facility, the percentage that the lift is helping hold the patient up, the daily usage (i.e., in minutes), whether or not the lift motor needs to be checked, whether service is needed, the distance a patient is ambulated, a lift lifetime indicator, the number of times the lift and/or the sling being used was overloaded, the lift use time, the time since the lift was last serviced, the number of times the service indicator was reset, and the last time an inspection was performed.

Figure 23:
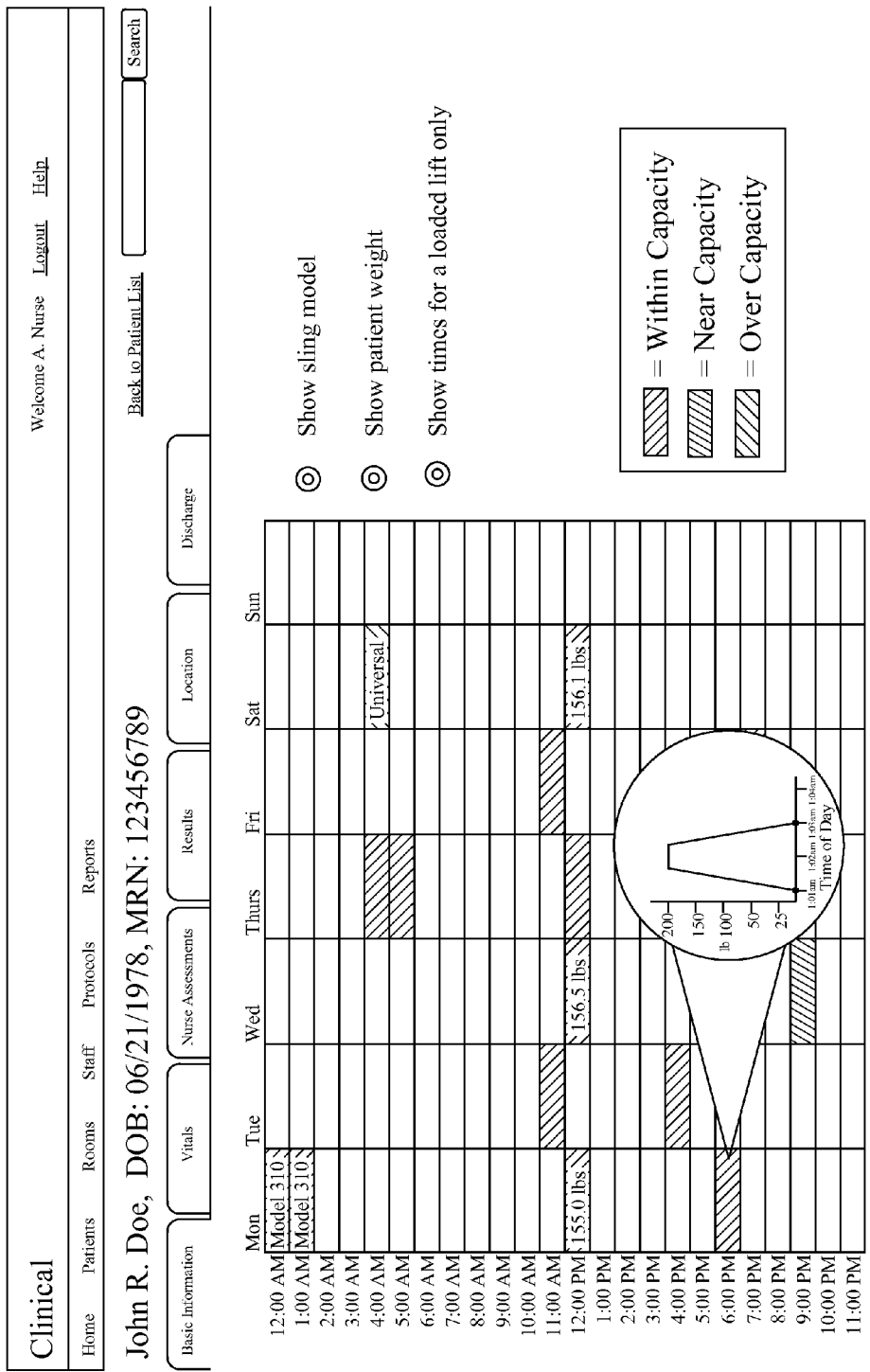
FIG. 23 is a screen shot of the interface to the workflow automation system of FIG. 1 showing the patients tab, which displays the date and time the lift was used along with the model of the sling, the weight of the person, and/or a predefined alert.

If the user selects the link corresponding to the patient information, a second screen is displayed with information about equipment used with the patient, the patient's vitals, the nurse assessments, any test results, the person's location, and discharge information as shown in FIG. 23. The information about the equipment used with the patient is shown in a chart that indicates the times the lift was used and what day of the week the use occurred, the model of the sling 53 that was used during that time (if any), the weight of the person if the lift was used to weigh them. In some contemplated embodiments, the chart can show whether the sling 53 was small, medium, or large instead of the model. In some contemplated embodiments, the chart can identify the caregiver that used the lift. The chart can be color coded to show when the lift was not in use and when the load experienced by the lift was within capacity, near capacity, or over capacity. The information displayed in the chart can be filtered so that the user can selectively display the sling model, the patient weight, or only the uses where the lift was loaded.

Figure 24:
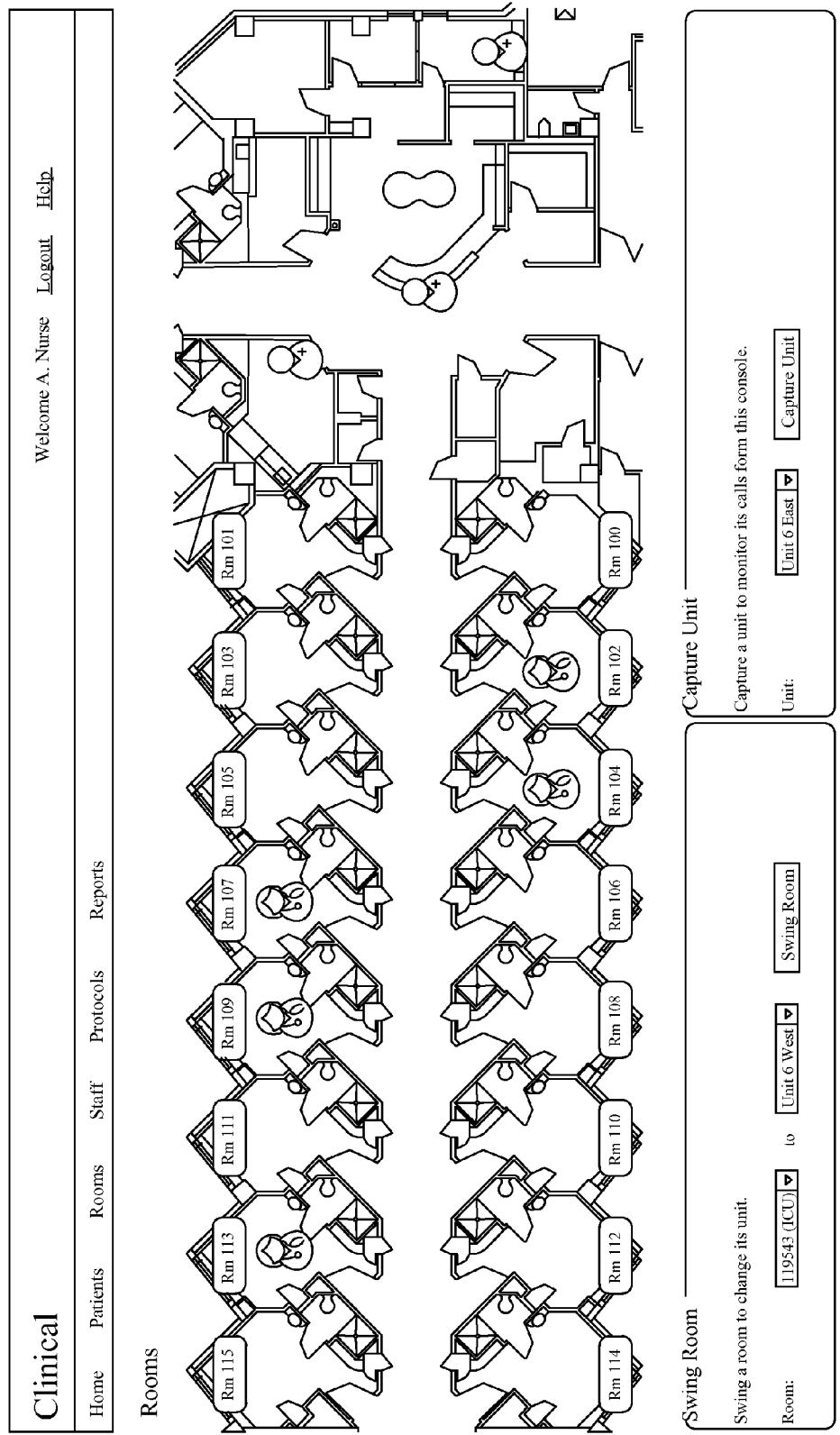
FIG. 24 is a screen shot of the interface to the workflow automation system of FIG. 1 showing the room tab, which displays the status of various rooms and the locations of caregivers and objects in a designated section of a care facility.

If the user selects the link corresponding to the room information, a third screen is displayed with information about the location of the caregivers in the wing or unit of the care facility, the status of the rooms, and the presence or absence of equipment in the room as shown in FIG. 24. In some contemplated embodiments, when a patient is admitted, a caregiver can utilize this view to locate a room that is vacant with the appropriate equipment in it. In some contemplated embodiments, the caregiver can assign a person to a room and assign equipment to be placed in the room so that it can be placed in the room before the patient gets to the room or shortly there after.

If the user selects the link corresponding to the care facility's care protocols, a fourth screen is displayed with various alert and reminder options for the lifts and slings along with options for how and to whom the alert and/or reminder is to be communicated as shown in FIG. 25. The alert and reminder options for the lifting assembly 12 include: alert when battery status is below a predetermined charge threshold (i.e., 10% remaining), alert if service is overdue by a predetermined amount of time (i.e., 7 days, alert if a predetermined percent of the safe working load has been exceeded (i.e., 80%), alert if emergency cord is activated, remind service is due in a predetermined amount of time (i.e., 3 weeks), and alert when lift or the lift strap needs to be been cleaned. The caregiver can select whether they want to automatically assign the alerts and/or reminders to all the lifts in the care facility wing or unit, and whether they want the alert (i.e., for the emergency cord being activated) to be communicated to a group of people, a specific person, and/or through a Nurse Call system. In some contemplated embodiments, the care facility's protocols can automatically cause specific alerts to be assigned. In some contemplated embodiments, if the caregiver does not automatically assign the selected alerts and/or reminders to the lifts, the caregiver can manually assign the alert and/or reminder to each lift using the user interface on the lift. In some contemplated embodiments, maintenance reminders can be included (i.e., check the strap 26 for wear). In some contemplated embodiments, reminders to perform an assessment (i.e., lift assessment every 12 hour) or a therapy (turn the patient) can be displayed. In some contemplated embodiments, the reminders for performing assessments and therapies can be displayed on a display in the patient's room or on the display connected to the equipment (i.e., the lift or the bed). The alerts and reminders for the sling 53 include: alert if not in room for a predetermined amount of time (i.e., 2 days, alert if past lifetime expectancy by a predetermined amount of time (i.e., 6 months), alert if wrong sling used (which can be detected if/when a sling is associated with the lift as described below with respect to the RFD reader and tags), and remind when periodic inspection is due. The caregiver can select whether or not they want to automatically assign the alerts and reminders for the slings 53, show the location of the nearest sling, and automatically notify a group.

If the user selects the link corresponding to the reports, a fifth screen is displayed with a list of the reports that have been created by the caregiver, care facility, or manufacturer, along with some information about each of the reports as shown in FIG. 26. In one contemplated embodiment, the information about the reports can include a title, description, the last time the report was run, the person who the report is sent to (i.e., notification list), the frequency the report is scheduled to run (i.e., weekly), the day the report is scheduled to run (i.e., Monday), and the time the report is scheduled to run. Each report includes a link that allows the user to view and/or edit the report. The reports can be defined to provide caregivers and care facility administrators with information about a number of topics, including, rehabilitation progress for the patient, the amount of time the caregivers spend with the patients, the percentage of time the assigned protocols and/or hospital care protocols are complied with (i.e., the number of times a lift is used when a protocol proscribes a lift to be used), the total amount of weight lifted by the lifts over a given period of time for a given care facility wing or unit. In another contemplated embodiment, a report can be included that can chart the usage of the lifts and locations of the lifts to determine how many lifts are needed in a given area.

Many other embodiments of the present disclosure are also envisioned. In one example, an equipment associating system, comprises an electronic tag 74 coupled to an asset; a person lift system 12 including an electronic reader 82 configured to read the electronic tag 74 when the electronic tag 74 is a predetermined distance from the electronic reader 82; and an information management system 18 configured to receive information from the person lift system 12 corresponding to the electronic tag 74 and to associate the asset and the person lift system 12. In one contemplated embodiment, the asset is a patient. In another contemplated embodiment, the asset is a medical device. In another contemplated embodiment, the asset is a person support structure 14. In another contemplated embodiment, the asset is a person's medication. In another contemplated embodiment, the asset is a caregiver. In another contemplated embodiment, the information management system 18 includes an asset tracking feature. In another contemplated embodiment, the person lift system 12 includes a motor 58, a tether 50 configured to be extended and retracted by the motor 58, and a sling support 52 coupled to the tether 50, wherein the electronic reader 82 is coupled to the sling support 52. In another contemplated embodiment, the electronic reader 82 is an RFID reader and the electronic tag 74 is an RFID tag. In another contemplated embodiment, the electronic reader 82 is configured to write information to the electronic tag 74. In another contemplated embodiment, the electronic reader 82 writes information corresponding to at least one of the condition of the asset, the status of the asset, the performance of the asset, and the association of an asset with another asset. In another contemplated embodiment, the predetermined distance is about 3 feet from the electronic reader 82. In another contemplated embodiment, the person lift system 12 communicates the information wirelessly to a communication system 16 in communication with the information management system 18. In another contemplated embodiment, the person lift system 12 includes a rail 38 coupled to a ceiling of a room and a lift assembly 40 movable along the rail 38. In another contemplated embodiment, the rail 38 includes electrical conductors 46 configured to provide at least one of data and power communication to the lift assembly 40.

In another example, a patient lift system movably coupled to a ceiling of a room, comprises a lift motor; and a tether configured to be extended and retracted by the lift motor, the tether including a plurality of symbols spaced apart a fixed distance and extending along the length of the tether.

In another example, a lift system comprises a lift motor; a tether configured to be extended and retracted by the lift motor and including a plurality of symbols thereon; a sensor configured sense the symbols on the tether and generate a signal corresponding to the symbols as the tether moves with respect to the sensor; and a control system configured to control the operation of the motor and to determine a movement characteristic of the tether as a function of the signal from the sensor. In another contemplated embodiment, the control system determines the speed the tether is moving as a function of the signal from the sensor. In another contemplated embodiment, the control system determines the direction the tether is moving as a function of the signal from the sensor. In another contemplated embodiment, the control system determines the distance the tether has moved as a function of the signal from the sensor. In another contemplated embodiment, the symbols include a first line having a first length, a second line having a second length and a third line having a third length, wherein the first length, the second length, and the third length are all different lengths. In another contemplated embodiment, the symbols include grey scale coding. In another contemplated embodiment, the symbols are located on an edge of the tether.

In another example, a lift system comprises a lift motor including a motor shaft having a plurality of symbols thereon; a tether configured to be extended and retracted by the lift motor; a sensor configured sense the symbols on the motor shaft and generate a signal corresponding to the symbols as the motor shaft moves with respect to the sensor; and a control system configured to control the operation of the motor and to determine a movement characteristic of the tether as a function of the signal from the sensor. In one contemplated embodiment, the control system determines the speed the tether is moving as a function of the signal from the sensor. In another contemplated embodiment, the control system determines the direction the tether is moving as a function of the signal from the sensor. In another contemplated embodiment, the control system determines the distance the tether has moved as a function of the signal from the sensor. In another contemplated embodiment, the symbols include grey scale coding.

In another example, a lift system comprises a lift motor; a tether configured to be extended and retracted by the lift; and a sensor configured sense the condition the tether as the tether moves with respect to the sensor. In another contemplated embodiment, the lift system further comprises a control system configured to control the operation of the motor and to determine when the tether requires servicing. In another contemplated embodiment, the control system alerts a user when the tether requires servicing. In another contemplated embodiment, the sensor includes an optical sensor. In another contemplated embodiment, the lift system is movably coupled to a ceiling of a room.

In another example, a lift system comprises a lift motor; a tether configured to be extended and retracted by the lift motor; a sling support coupled to the tether and configured to support a sling; and an electronic reader coupled to the sling support and configured to sense electronic tags within a predetermined area. In another contemplated embodiment, the lift system is movably coupled to a ceiling of a room. In another contemplated embodiment, the electronic reader and electronic tags include a radio frequency identification reader and radio frequency identification tags. In another contemplated embodiment, the lift system is configured to communicate information corresponding to the electronic tags that the electronic reader senses within the predetermined area to an information management system. In another contemplated embodiment, the information management system associates assets that the electronic tags are coupled to. In another contemplated embodiment, the assets include at least one of a sling, a caregiver, a patient, medicine, and a person support structure. In another contemplated embodiment, the predetermined area extends about three feet from the electronic reader. In another contemplated embodiment, the electronic tags include information corresponding to at least one of the model number, performance characteristics, and size. In one contemplated embodiment, the lift system is movably coupled to a ceiling of a room. In another contemplated embodiment, the electronic reader and electronic tags include a radio frequency identification reader and radio frequency identification tags. In another contemplated embodiment, the lift system is configured to communicate information corresponding to the electronic tags that the electronic reader senses within the predetermined area to an information management system. In another contemplated embodiment, the information management system associates assets that the electronic tags are coupled to. In another contemplated embodiment, the assets include at least one of a sling, a caregiver, a patient, medicine, and a person support structure. In another contemplated embodiment, the predetermined area extends about three feet from the electronic reader. In another contemplated embodiment, the electronic tags include information corresponding to at least one of the model number, performance characteristics, and size. Wherein the electronic reader and electronic tags include a radio frequency identification reader and radio frequency identification tags. In another contemplated embodiment, the lift system is configured to communicate information corresponding to the electronic tags that the electronic reader senses within the predetermined area to an information management system. In another contemplated embodiment, the information management system associates assets that the electronic tags are coupled to. In another contemplated embodiment, the assets include at least one of a sling, a caregiver, a patient, medicine, and a person support structure. In another contemplated embodiment, the predetermined area extends about three feet from the electronic reader. In another contemplated embodiment, the lift assembly includes a lift, a tether configured to be extended and retracted from the lift, and a sling support coupled to the tether, wherein the electronic reader is coupled to the sling support. In another contemplated embodiment, the electronic reader is configured to write to the electronic tags. In another contemplated embodiment, the electronic reader stores at least one of performance information corresponding to the asset, association information, facility information, asset condition and status. In another contemplated embodiment, the lift system further comprising a control system configured to control the lift assembly, the control system receiving information corresponding to a sling sensed by the electronic reader and determining if the sling is approved for use with a specific person. In another contemplated embodiment, the control system alerts a user if the sling is one of unapproved for use with the person and unknown. In another contemplated embodiment, the lift assembly is movably coupled to a ceiling of a room.

In another example, a monitoring system, comprises a lift assembly configured to lift a patient; a sling configured to be removably coupled to the lift assembly; a control system configured to control operation of the lift assembly; and a reporting system in communication with the control system and configured to receive operational information for the lift assembly, the reporting system being configured to determine if the operation of the lift assembly is in compliance with a protocol. In one contemplated embodiment, the reporting system is part of a control system for a person support structure. In another contemplated embodiment, the reporting system generates an alert if the operation of the lift system is not in compliance with the protocol. In another contemplated embodiment, the operational information corresponds to a lift event which is determined as a function of the engagement status of a lifting sling with the lift assembly. In another contemplated embodiment, the operational information corresponds to a lift event which is determined as a function of the distance the sling has been moved. In another contemplated embodiment, the operational information corresponds to a lift event which is determined as a function of the weight of a person supported on the lift assembly. In another contemplated embodiment, the operational information corresponds to a lift event which is determined as a function of the amount of time the lift assembly was being used. In another contemplated embodiment, the operational information corresponds to a lift event which is determined as a function of the amount of current used to power a lift motor of the lift assembly. In another contemplated embodiment, the operational information corresponds to a lift event which is determined as a function of the duration an input on a user interface of the control system was pressed and held. In another contemplated embodiment, the lift assembly comprises a motor, a tether configured to be extended and retracted by the motor, and a sling bar coupled to the tether and configured to removably retain the sling. In another contemplated embodiment, the sling bar includes a retaining element and a sensor configured to sense when the retaining element is configured to allow a sling to be attached to the sling bar. In another contemplated embodiment, the sensor includes a load cell configured to sense the amount of force exerted on the sling bar by the sling. In another contemplated embodiment, the sensor includes a contact sensor that is in a first state when the retaining element is closed and in a second state when the retaining element is opened to allow a sling to be coupled to the sling bar. In another contemplated embodiment, the sling bar includes a retaining element and a sensor configured to sense when the sling is retained by the retaining element. In another contemplated embodiment, the sensor includes a hall-effect sensor. In another contemplated embodiment, the sensor includes an optical sensor. In another contemplated embodiment, the sensor includes an electronic reader configured to read an electronic tag coupled to the sling. In another contemplated embodiment, the control system is configured to determine when a non-approved sling is being used with the lift system based the information stored on an electronic tag. In another contemplated embodiment, the control system is configured to determine when a non-approved sling is being used with the lift system based on the absence of an electronic tag. In another contemplated embodiment, the electronic tag includes information corresponding to at least one of the sling model number, performance characteristics, and the size of the sling. In another contemplated embodiment, the sensor includes a magnetic sensor that is configured to sense a magnet coupled to the sling. In another contemplated embodiment, the reporting system generates an alert if the lift assembly is not being used in compliance with the protocol. In another contemplated embodiment, the reporting system communicates whether the lift assembly was used in compliance with the protocol to an electronic medical record. In another contemplated embodiment, the reporting system receives information from an electronic medical record corresponding to whether or not the occupant is required to be lifted using the lift assembly. In another contemplated embodiment, a lift event has occurred when the sling is coupled to the lift assembly and subsequently uncoupled from the lift assembly. In another contemplated embodiment, a lift event has occurred when the sling is coupled to the lift assembly, the lift assembly is operated, and the sling is uncoupled from the lift assembly. In another contemplated embodiment, the operation of the lift assembly is determined as a function of the amount of time the lift assembly was operated. In another contemplated embodiment, the lift assembly includes a motor and operation of the lift assembly is determined as a function of the amount of current used to power the motor. In another contemplated embodiment, the control system includes a user interface with a plurality of inputs and operation of the lift assembly is determined as a function of the duration the inputs were pressed and held. In another contemplated embodiment, the lift assembly includes a motor and a tether that is configured to be extended and retracted by the motor, operation of the lift assembly is determined as a function of the distance the tether is moved. In another contemplated embodiment, the distance the tether is moved is determined using a potentiometer. In another contemplated embodiment, the distance the tether is moved is determined using an optical sensor configured to sense patterns on the tether as the tether moves with respect to the sensor. In another contemplated embodiment, the patterns include three lines of increasing length extending across the width of the tether. In another contemplated embodiment, the reporting system receives at least one of date and time information from an asset locating and tracking system.

In another example, a person support lifting system, comprises a lift assembly configured to lift a person; a sensor coupled to the lift assembly and configured to sense the load generated by the person and supported by the lift assembly; a control system electrically coupled to the sensor and configured to display the load supported by the lift assembly over a period of time on a display device.

In another example, a system for associating assets, comprises a lift assembly configured to lift a patient; an identifying device coupled to an asset; a reading device coupled to the lift assembly and configured to read the identifying device; and a control system configured to associate the lift assembly and the asset when the asset is less than a predetermined distance from the reading device. In one contemplated embodiment, the lift assembly is an overhead lift with a tether that extends from the lift, the reader being coupled to the tether. In another contemplated embodiment, the asset includes a caregiver. In another contemplated embodiment, the asset includes a sling. In another contemplated embodiment, the asset includes a patient. In another contemplated embodiment, the asset includes a hospital bed.

In another example, a method of determining when a lift event occurred, comprising the steps of: sensing when a sling has been coupled to a person lifting device; and sensing when a sling has been decoupled from the person lifting device. In one contemplated embodiment, the step of sensing if the lifting device was operated before the sling was decoupled from the lifting device.

In another example a method, comprises the steps of: determining if an occupant supported on a person support system has moved from a first position to a second position with respect to the person support system; determine if a lifting device is required to move the person; determine if a caregiver was within a predetermined distance of the occupant when the movement occurred; and indicate a lift compliance status. In another contemplated embodiment, the status is compliant if the lifting device was required to be used and the occupant moved from the first position to the second position and the caregiver was within the predetermined distance and the lifting device was operated. In another contemplated embodiment, the status is compliant if the lifting device was not required to be used. In another contemplated embodiment, the status is non-compliant if the lifting device was required to be used and the occupant moved from the first position to the second position and the caregiver was within the predetermined distance and the lifting device was not operated. In another contemplated embodiment, the status is compliant if the lifting device was required to be used and the occupant moved from the first position to the second position and the caregiver was not within the predetermined distance.

In another example, a sling assembly, comprises a sling; and an RFID tag coupled to the sling.

In another example, an information display system, comprises an information management system including information corresponding to a person support structure and a person lift system; and a display configured to simultaneously display the information corresponding to the person support structure and the person lift system communicated to the display by the information management system. In one contemplated embodiment, the information management system includes a processor and memory configured to store the information corresponding to the person support structure and the person lift system. In another contemplated embodiment, the information management system also stores information corresponding to resources including at least one of a care facility, the care facility's staff, the care facility's protocols, the patient's in the care facility and the equipment in the care facility. In another contemplated embodiment, the information corresponding to the resources is displayed on the display.

In another example, a system, comprises an information management system; a person lifting device including a control system configured to control the operation of the person lifting device and to communicate information corresponding to at least one of the person lifting device and a person being lifted by the person lifting device to the information management system; and a person support device including a control system configured to control the operation of the person support device and to communicate information corresponding to at least one of the person support device and the person supported on the person support device to the information management system. In another contemplated embodiment, the information management system includes a work-flow automation feature. In another contemplated embodiment, the information management system includes an electronic medical record system. In another contemplated embodiment, the information management system includes a real time locating system. In another contemplated embodiment, the information management system includes a compliance feature. In another contemplated embodiment, the information management system includes a caregiver communication feature. In another contemplated embodiment, the control system of the person lifting device includes a communication device configured to communicate the information via a wired connection. In another contemplated embodiment, the control system of the person lifting device includes a communication device configured to communicate the information over a power connection. In another contemplated embodiment, the control system of the person lifting device includes a communication device configured to communicate the information via a fiber-optic connection. In another contemplated embodiment, the control system of the person lifting device includes a communication device configured to communicate the information via a wireless connection. In another contemplated embodiment, the control system of the person lifting device includes a communication device configured to communicate the information via a LIN bus. In another contemplated embodiment, the control system of the person lifting device includes a communication device configured to communicate the information via a bluetooth connection. In another contemplated embodiment, the control system of the person lifting device includes a communication device configured to communicate the information using near field communication. In another contemplated embodiment, the information received by and stored on the information management system is displayed on a user interface. In another contemplated embodiment, the user interface includes a display coupled to a pendant. In another contemplated embodiment, the user interface includes a mobile device display. In another contemplated embodiment, the user interface includes a display coupled to the person support structure. In another contemplated embodiment, the user interface includes a terminal at a nurse station. In another contemplated embodiment, the data corresponding to the person support device and the person lifting device are displayed. In another contemplated embodiment, the person lifting device includes a rail coupled to a ceiling of a room and a lift assembly movable along the rail, the rail including conductors extending therealong that are contacted by the lift assembly and configured to communicate at least one of data and power between the information management system and the control system of the person lifting device.

In another example, a system, comprises an information management system; a person support device including a control system configured to control the operation of the person support device and to communicate information corresponding to at least one of the person support device and the person supported on the person support device to the information management system; and a person lifting device including a control system configured to control the operation of the person lifting device and to communicate information corresponding to at least one of the person lifting device and a person being lifted by the person lifting device to the information management system via the person support device. In one example, a person support device communicates with the information management system through a communication system. In another contemplated embodiment, the person support device includes a person support surface. In another contemplated embodiment, the person support surface includes at least one fluid bladder configured to be supplied by a fluid supply. In another contemplated embodiment, the person support device includes a lower frame movably supported above a lower frame by a lift mechanism coupled to the lower frame. In another contemplated embodiment, the control system of the person support device person support device is configured to determine when an occupant has egressed from the person support device. In another contemplated embodiment, the control system of the person support device is configured to calculate the center of gravity of a person supported on the person support device. In another contemplated embodiment, the information management system includes a work-flow system. In another contemplated embodiment, the information management system includes an electronic medical record system. In another contemplated embodiment, the information management system includes an asset tracking system. In another contemplated embodiment, the control system of the person lifting device includes a communication device configured to communicate the information via a wired connection. In another contemplated embodiment, the control system of the person lifting device includes a communication device configured to communicate the information over a power connection. In another contemplated embodiment, the control system of the person lifting device includes a communication device configured to communicate the information via a fiber-optic connection. In another contemplated embodiment, the control system of the person lifting device includes a communication device configured to communicate the information via a wireless connection. In another contemplated embodiment, the control system of the person lifting device includes a communication device configured to communicate the information via a LIN bus. In another contemplated embodiment, the control system of the person lifting device includes a communication device configured to communicate the information via a bluetooth connection. In another contemplated embodiment, the control system of the person lifting device includes a communication device configured to communicate the information using near field communication. In another contemplated embodiment, the information received by and stored on the information management system is displayed on a user interface. In another contemplated embodiment, the user interface includes a display coupled to a pendant. In another contemplated embodiment, the user interface includes a mobile device display. In another contemplated embodiment, the user interface includes a display coupled to the person support structure. In another contemplated embodiment, the user interface includes a terminal at a nurse station. In another contemplated embodiment, the data corresponding to the person support device and the person lifting device are displayed In another example, a person support system comprises a person lifting system configured to lift a person; a person support structure configured to support a person thereon; a controller including a processor and memory storing instructions that, when acted upon by the processor, cause the processor to determine when an occupant egresses from the person support structure and if the person lifting system was operated. In one contemplated embodiment, the processor determines that an occupant egressed from the person support structure as a function of a change in the occupant's center of gravity. In another contemplated embodiment, the processor determines that an occupant egressed from the person support structure as a function of a change in a pressure profile of the occupant. In another contemplated embodiment, the instructions further cause the controller to determine if the occupant was required to be moved using a person lifting system In another example, a monitoring system comprises a locating system; a person support structure configured to support a person thereon; a reporting system in communication with the locating system and the person support structure and configured to receive person movement information from the person support structure and caregiver location information from the locating system, the reporting system being configured to determine if a lift event occurred based on the location of a caregiver and a person's movement with respect to the person support structure. In one contemplated embodiment, the reporting system and locating system are incorporated into a control system configured to control the operation of the person support structure. In another contemplated embodiment, the person movement information includes a change in a person's center of gravity with respect to the person support structure. In another contemplated embodiment, the reporting system determines that a lift event occurred when a caregiver is located proximate to the person support structure and a person supported on the person support structure moves. In another contemplated embodiment, the reporting system receives information corresponding to operational information from a person lifting device and information corresponding to whether the person on the person support structure is required to be moved with a person lifting device to determine if the lift event was compliant. In another contemplated embodiment, the reporting system determines that a lift event is compliant when the person supported on the person support structure is required to be moved by a person lifting device and the operational information from the lifting device indicates that the person lifting device was being operated while the person was moving. In another contemplated embodiment, the reporting system receives the information corresponding to whether the person on the person support structure is required to be moved using a person lifting device from an electronic medical record system. In another contemplated embodiment, the operational information corresponds to the engagement status of a lifting sling with the lift assembly. In another contemplated embodiment, the operational information corresponds to the distance the sling has been moved. In another contemplated embodiment, the operational information corresponds to the weight of a person supported on the lift assembly. In another contemplated embodiment, the operational information corresponds to the lift assembly was being used. In another contemplated embodiment, the operational information corresponds to the amount of current used to power a lift motor of the lift assembly. In another contemplated embodiment, the operational information corresponds to the duration an input on a user interface of the control system was pressed and held. In another contemplated embodiment, the person lifting device includes track coupled to a ceiling of a room and a lift assembly configured to move along the track, the lift assembly including a lift motor, a tether, and a sing support.

In another example, a monitoring system, comprises a lift assembly configured to lift a person; a person support structure configured to support a person thereon; and a reporting system in communication with the lift assembly and the person support structure and configured to receive operational information from the lift assembly and person movement information from the person support structure, the reporting system being configured to determine if a lift event occurred based on person movement information received from the person support structure and operational information received from the lift assembly. In one example, the person movement information corresponds to a change in the person's center of gravity on the person support structure. In another contemplated embodiment, the reporting system is part of a control system configured to control at least one function of the person support structure. In another contemplated embodiment, the person movement information corresponds to a change in the person's pressure profile sensed by a pressure sensing system. In another contemplated embodiment, the reporting system receives information indicative of the patient's requirement to be lifted.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described may be more desirable, it nonetheless may not be necessary and embodiments lacking the same may be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item may include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, the same are to be considered as illustrative and not intended to be exhaustive or to limit the disclosure to the precise forms disclosed. Additional alternatives, modifications and variations may be apparent to those skilled in the art. Also, while multiple inventive aspects and principles may have been presented, they need not be utilized in combination, and various combinations of inventive aspects and principles are possible in light of the various embodiments provided above.

What is claimed is:

1. A monitoring system comprising:
a person support structure configured to support a person thereon;
a person lifting system configured to lift a person to change the person's position with respect to the person support structure; and
a reporting system configured to indicate whether a lift event is compliant as a function of a change in position of a person on the person support structure, a requirement that the person be moved using the person lifting system, a caregiver's presence, and usage of the person lifting system.

2. The monitoring system of claim 1, wherein the reporting system is part of a control system configured to control the operation of the person support structure.

3. The monitoring system of claim 1, wherein the change in position is determined using the person's center of gravity.

4. The monitoring system of claim 1, wherein the change in position is determined using the person's sensed pressure profile.

5. The monitoring system of claim 1, wherein the caregiver's presence is provided by a locating system.

6. The monitoring system of claim 1, wherein the requirement that the person must be moved using a person lifting system is provided by an electronic medical record system.

7. The monitoring system of claim 1, wherein the reporting system indicates that a lift event is compliant when there is a change in position of a person on the person support structure, the person is required to be moved using the person lifting system, the caregiver is present about the time the change in position occurs, and the person lifting system is in use about the time the change in position occurs.

8. The monitoring system of claim 1, wherein the person lifting system includes a lift assembly and a sling, usage of the person lifting system is determined as a function of the engagement status of the sling with the lift assembly.

9. The monitoring system of claim 1, wherein the person lifting system includes a sling, usage of the person lifting system is determined as a function of the distance the sling is been moved.

10. The monitoring system of claim 1, wherein the person lifting system includes a sling, usage of the person lifting system is determined as a function of the weight of a person supported on the person lifting system.

11. The monitoring system of claim 1, wherein the person lifting system includes a lift motor, usage of the person lifting system is determined as a function of the amount of current used to power the lift motor.

12. The monitoring system of claim 1, wherein the person lifting system includes a user interface including at least one input, usage of the person lifting system is determined as a function of the duration an input is activated.

13. The monitoring system of claim 1, wherein the person lifting system includes track coupled to a ceiling of a room and a lift assembly configured to move along the track.

14. The monitoring system of claim 1, wherein the reporting system generates an alert if the lift event is not compliant.

15. The monitoring system of claim 1, wherein the reporting system communicates whether the lift event was compliant to an electronic medical record system.

\* \* \* \* \*